United States Patent
Dubey et al.

(10) Patent No.: US 12,167,731 B2
(45) Date of Patent: Dec. 17, 2024

(54) FUNGICIDES TO PREVENT AND CONTROL FUNGAL PATHOGENS

(71) Applicant: UNIVERSITÉ DE LAUSANNE, Lausanne (CH)

(72) Inventors: Olga Dubey, Préverenges (CH); Edward Farmer, Bussigny (CH); Christiane Nawrath, Lausanne (CH); Katia Gindro, Nyon (CH); Sylvain Schnee, Nyon (CH); Sylvain Dubey, Préverenges (CH)

(73) Assignee: UNIVERSITE DE LAUSANNE, Lausanne (CH)

( * ) Notice: Subject to any disclaimer, the term of this patent is extended or adjusted under 35 U.S.C. 154(b) by 543 days.

(21) Appl. No.: 17/259,228

(22) PCT Filed: Jul. 9, 2019

(86) PCT No.: PCT/EP2019/068336
§ 371 (c)(1),
(2) Date: Jan. 11, 2021

(87) PCT Pub. No.: WO2020/011750
PCT Pub. Date: Jan. 16, 2020

(65) Prior Publication Data
US 2021/0259251 A1 Aug. 26, 2021

(30) Foreign Application Priority Data
Jul. 9, 2018 (EP) ..................... 18182433

(51) Int. Cl.
| | | |
|---|---|---|
| A01N 47/46 | (2006.01) | |
| A61K 8/46 | (2006.01) | |
| A61K 9/00 | (2006.01) | |
| A61K 31/26 | (2006.01) | |
| A61P 31/10 | (2006.01) | |
| A61Q 11/00 | (2006.01) | |

(52) U.S. Cl.
CPC .............. *A01N 47/46* (2013.01); *A61K 8/466* (2013.01); *A61K 9/0056* (2013.01); *A61K 31/26* (2013.01); *A61P 31/10* (2018.01); *A61Q 11/00* (2013.01)

(58) Field of Classification Search
CPC .......... A01N 47/46; A61K 6/52; A61K 31/26; A61K 2300/00; A61P 31/10; A01P 3/00
See application file for complete search history.

(56) References Cited

FOREIGN PATENT DOCUMENTS

| | | | |
|---|---|---|---|
| DE | 1793450 A1 | | 7/1971 |
| JP | 11246319 | * | 9/1999 |
| JP | 2008115133 | * | 5/2008 |

OTHER PUBLICATIONS

Database WPI Week 199948 Thomas Scientific, London, GB; An 1999-566392 XP002785404.
K. Gilliver, "The Inhibitory Action of Antibiotics on Plant Pathogenic Bacteria and Fungi", Annals of Botany, N.S. vol. X, No. 39, pp. 271-282, Jul. 1946.
T. Sotelo et al., "In Vitro Activity of Glucosinolates and Their Degradation Products against *Brassica*—Pathogenic Bacteria and Fungi", Applied and Environmental Microbiology, vol. 81, No. 1, pp. 432-440, 2015.
L. Drobnica et al., "Antifungal Activity of Isothiocyanates and Related Compounds" Applied Microbiology, vol. 15, No. 4, pp. 701-709, 1967.
Aug. 22, 2019 International Search Report issued in International Patent Application No. PCT/EP2019/068336.
Aug. 22, 2019 Written Opinion issued in International Patent Application No. PCT/EP2019/068336.
Jul. 13, 2020 International Preliminary Report on Patentability issued in International Patent Application No. PCT/EP2019/068336.

* cited by examiner

*Primary Examiner* — Lezah Roberts
(74) *Attorney, Agent, or Firm* — Oliff PLC

(57) ABSTRACT

A field of biological fungicides with a broad range of antifungal activity coming from plant extracts from the order of Brassicales or molecules revealing similar chemical structure. In particular, Applicants surprisingly provided a new usage of a combination of sulfonyl and sulfinyl containing aliphatic glucosinolates, their by-products and synthetic analogues as efficient antifungal compounds with broad spectrum of activity.

8 Claims, 1 Drawing Sheet

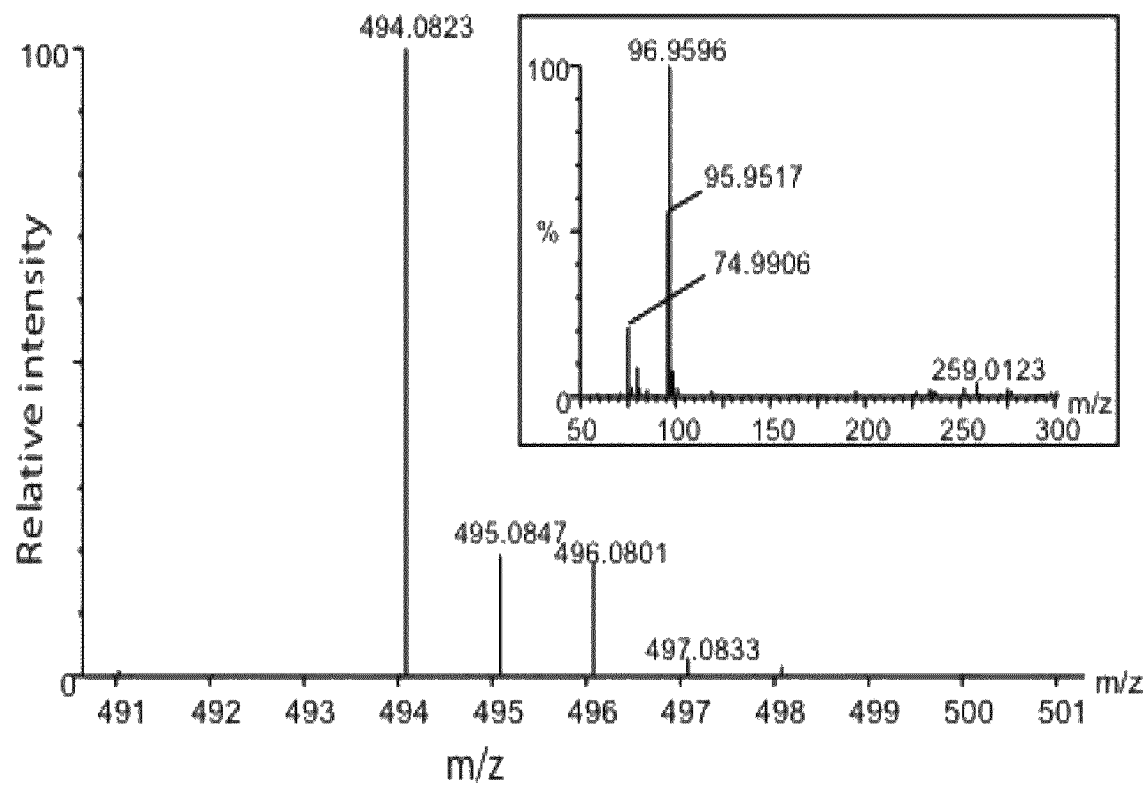
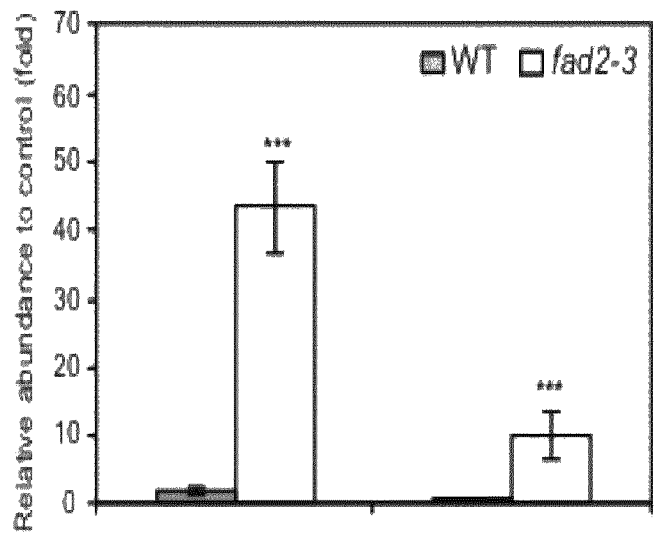
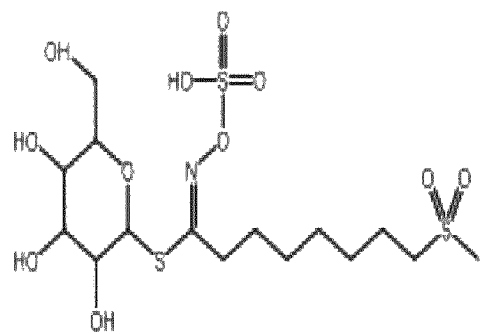

FUNGICIDES TO PREVENT AND CONTROL FUNGAL PATHOGENS

FIELD OF THE INVENTION

The invention relates to the field of biological fungicides with a broad range of antifungal activity coming from plant extracts from the order of Brassicales or molecules revealing similar chemical structure. In particular, Applicants surprisingly provided a new usage of a combination of sulfonyl and sulfinyl containing aliphatic glucosinolates, their by-products and synthetic analogues as efficient antifungal compounds with broad spectrum of activity.

BACKGROUND OF THE INVENTION

Human population is increasing each year and is about to reach 8.6 billion by 2030. To maintain high levels of food production farmers have to use external treatments, such as: 1) chemical pesticides that have high efficiency, accessible costs, but reveal negative impact on the environment and human health; 2) biological pesticides having no harmful effect on environment, but showing low efficiency (less than 60%, compared to existing chemical pesticide) and high costs. That makes biological pesticides not accessible for many countries and opens possibilities to develop and bring to market novel organic treatments that reveal high efficiency and accessible costs and are environmentally friendly.

In the last decades, some biological approaches were developed to prevent *B. cinerea* in the field, e.g. the application of *Bacillus subtilis* and *Trichoderma harzanium*, but they are poorly used in farming due to their low efficiency.

In western European agriculture, the commonly used bio-preventive fungicides are copper and sulphur. These fungicides are costly to apply due to the need to reapply after each precipitation. In addition, high concentrations of these metals in soil have negative impacts on the environment.

As a consequence, there is a need to provide an alternative to these techniques, by being more respectful towards the environment, as well as a highly efficient preventive treatment against fungal pathogens.

Plant fungal pathogens are one of the agronomical treats that lead to severe food loses yearly. The efficiency of fungal pathogens is caused by their easy dispersal in nature, rapid attachment on the host surface and fast germ tube development that promotes penetration in plants. Plants, on the other hand, have developed several defence mechanisms against fungal pathogens e.g. necrotrophs: a) prevention of pathogen penetration; b) increased levels of reactive oxygen species; c) induction of defence hormones, such as jasmonate, ethylene, salicylic and abscisic acid. Additionally, some plants are synthetizing fungitoxic compounds that prevent fungal development on plant surface and stop disease formation. Identification of plant compounds with strong antifungal activity can lead to development of novel biological fungicides that can, potentially, replace currently existing chemical treatments.

Order of Brassicales consists of economically important plants that are broadly distributed and used as food source. This group of plants was shown to have a unique set of secondary metabolites—glucosinolates. In the last decades glucosinolates were shown to have anti-cancerous, anti-inflammatory and insecticidal properties.

For example JPH11139949 A (OGAWA KORYO CO LTD) discloses how to obtain an antibacterial-antifungal agent free from strong irritating odour, having a high threshold, low in volatility and having an excellent antibacterial-antifungal activity by compounding a specific [omega]-alkenyl isothiocyanate compound or a specific [omega]-alkylthioalkyl isothiocyanate compound. An [omega]-alkenyl isothiocyanate compound having the formula: CH2 CH(CH2)m NCS [(m)=2-10] (e.g. 3-butenyl isothiocyanate) or an [omega]-alkylthioalkyl isothiocyanate compound having the formula: RS(CH2)n2 NCS [(n)=1-10; R is a 1-4C alkyl](e.g. methylthiomethyl isothiocyanate) is compounded in a food in an amount of 0.01-100 ppm, preferably 1-50 ppm or in an oral hygienic agent in a concentration of about 0.01-100 ppm.

Similarly, JPH11246319 A (OGAWA KORYO CO LTD) discloses how to obtain an antimicrobial and antifungal agent that can largely alleviate the irritating smell and can be applied to various kinds of beverage and food by using a specific [omega]-alkylsulfinylalkykl isothiocyanate as an active ingredient. This antimicrobial and antifungal agent comprises an [omega]-alkylsulfinylalkyl isothiocyanate represented by the formula: R—S(O)—(CH2)n —NCS (n is 1-10; R is a 1-4C alkyl). In an embodiment, this isothiocyanate is 3-methylsulfinylpropyl isothiocyanate, 6-methylsulfinyl-propyl isothiocyanate or the like. The compound in formula I where n is <=7 is included in the flavour components of horse radish, but its content is low. The compound of the formula is prepared by oxidizing [omega]-methylthioalkyl isothiocyanate of the formula: CH3 S—(CH2)n —NCS with a peroxide.

JP2000086414 A (KINJIRUSHI WASABI KK) discloses how to obtain an antimicrobial agent containing an aromatic component of horseradish as an active ingredient, esp. showing an antibacterial spectrum broadly ranging from fungi to bacteria, and exerting a strong bacteriostatic and antibacterial effect even with an infinitesimal content of the aromatic component. The agent comprises, as an active ingredient, an aromatic component of horseradish of n-methylsulfonylalkylisothiocyanate and one or more aromatic components of horseradish selected from the group consisting of n-methylthioalkyl isothiocyanate, n-methylsulfinylalkyl isothiocyanate, and allyl isothiocyanate. The agent comprises, as an active ingredient, aromatic components of horseradish of both n-methylthioalkyl isothiocyanate and n-methylsulfinylalkyl isothiocyanate.

K. GILLIVER "The Inhibitory Action of Antibiotics on Plant Pathogenic Bacteria and Fungi", ANNALS OF BOTANY, vol. 10, no. 3, 1 Jul. 1946 (1946-07-01), pages 271-282, XP55512767, GB ISSN: 0305-7364, DOI: 10.1093/oxfordjournals.aob.a083136; reports that example of antagonism between soil micro-organisms and plant pathogens have been recognized for many years; and in some instances biological methods of disease control have been elaborated. Specific antibiotic substances have been isolated from culture filtrates of fungi, bacteria and Actinomycetes, and some of them have been shown to have an antagonistic action against causal organisms of plant diseases. In particular, the antifungal activity of cheiroline is disclosed.

In T Sotelo et al. "In vitro activity of glucosinolates and their degradation products against *Brassica*-Pathogenic bacteria and fungi", Applied and Environmental Microbiology, 1 Jan. 2015 (2015-01-01), pages 432-440, XP55512754, DOI: 10.1128/AEM.03142-14, the objective of the work was to evaluate the biocide effects of 17 Glucosinolates (GSLs) and glucosinolate hydrolysis products (GHPs) and of leaf methanolic extracts of different GSL-enriched *Brassica* crops on suppressing in vitro growth of two bacterial (*Xanthomonas campestris* pv. *campestris* and *Pseudomonas* syringae pv. maculicola) and two fungal (*Alternaria brassicae* and *Sclerotinia scletoriorum*) *Brassica* pathogens. GSLs, GHPs, and methanolic leaf extracts inhibited the development of the pathogens tested compared to the control, and the effect was dose dependent. In particular, this document discloses the antifungal activity of sulorafane.

L DROBNICA et al. "Antifungal activity of Isothiocyanates and related compounds", APPLIED MICROBIOLOGY, vol. 15, no. 4, 1967, pages 701-709, presents the results of a study on the antifungal activity of isothiocyanates-derivatives of biphenyl (group "A"), of stilbene ("B"), of azobenzene and benzeneazonaphthalene ("C"), of naphthalene ("D"), and of further polycondensed aromatic hydrocarbons ("E"). From a total of 48 investigated compounds, antifungal activity was observed only in A and D group compounds. B, C, and E group derivatives are extremely insoluble in water, and the molecules are very large; as a result, they probably cannot pass into spores or mycelium of fungi. It was suggested that the —NCS group cannot manifest its reactivity. In particular, this document discloses the antifungal activity of of glucocheirolin, glucoerysolin and glucoberteroin.

DE 17 93 450 A1 (PHILIPS NV) relates to fungicidal compositions which contain certain thiocyanates, i.e. sulphinyl or sulphonyl-methylene rhodanides, and to methods for preparing and protecting plants against infestation by moulds.

However, there is still a need to provide molecules, being respectful towards the environment, but revealing a stronger fungitoxic effect and being active on a broader range of fungal pathogens.

BRIEF DESCRIPTION OF THE INVENTION

In the present invention, Applicants have identified a combination of sulfonyl and sulfinyl containing aliphatic glucosinolates revealing a strong fungitoxic effect on a broad range of fungal pathogens. This combination of products can be used as a new line of biological fungicides.

One of the objects of the present invention is to provide a use of a composition comprising the combination of at least two compounds selected from general formula I:

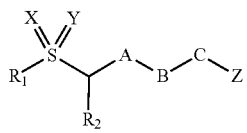

(I)

Wherein:
Z represents nitrile (—CN), thiocyanate (—SCN) or isothiocyanate (—N=C=S);
X, Y represent, independently of each other, a lone pair or O, with the proviso that at least one of the two X or Y is O;
$R_1$, $R_2$ represent, independently of each other, H, saturated linear, cyclic or branched ($C_1$-$C_6$)alkyl;
A, C represent, independently of each other, a covalent bond, saturated or unsaturated linear, cyclic, spirocyclic, bicyclic, polycyclic or branched ($C_1$-$C_8$)alkyl, $C_6$-aryl;
B represents, a covalent bond, saturated or unsaturated linear, cyclic, spirocyclic, bicyclic, polycyclic or branched ($C_1$-$C_8$)alkyl, $C_6$-aryl;

provided that at least one of A, B or C is different from a covalent bond, and characterized in that, the at least two combined compounds comprise:
1) at least one Z group representing isothiocyanate, and/or,
2) at least two different levels of oxidation of the sulphur atom, and/or,
3) at least a different length in the carbon chain residue -A-B-C-,
in the prevention or treatment of fungal pathogens in plants.

Another object of the present invention is to provide a composition comprising the combination of the compounds of the invention for use in a method for preventing or treating mycosis in human or animal patients.

A further object of the invention is to provide a fungicide composition comprising the combination of the compounds of the invention.

The present invention also relates to a food, a drink or an oral hygiene agent containing the above-mentioned antifungal agent, namely the fungicide composition.

Other objects and advantages of the invention will become apparent to those skilled in the art from a review of the ensuing detailed description, which proceeds with reference to the following illustrative drawings, and the attendant claims.

BRIEF DESCRIPTION OF THE FIGURES

FIG. 1: Represents newly identified secondary metabolite on the surface of fad2-3 cotyledons. (A) Characterization of 7-methylsulfonyl-heptyl-glucosinolate. An (M–H)⁻ ion at m/z 494.0823 corresponding to the molecular formula $C_{15}H_{29}NO_{11}S_3$ (calculated mass 494.0824, error 0.1 mDa) was observed. A major fragment ion at m/z 96.9599 typical of a sulfate moiety was also present. No known compound has been reported for the molecular formula $C_{15}H_{29}NO_{11}S_3$, however the obtained data strongly suggest this metabolite to be 7-methylsulfonyl-heptyl-glucosinolate, a new glucosinolate, which would be the 15-carbon analogue of 8-methylsulfonyl-octyl-glucosinolate ($C_{16}H_{31}NO_{11}S_3$). (B) Identification of a novel glucosinolate that was differentially abundant on the surface of WT and fad2-3 cotyledons and the first true leaves. Relative abundance of 7-methylsulfonyl-heptyl-glucosinolate in isopropanol washes from the surface of 7-day-old cotyledons and 14-day-old leafs. Error bars represent the means of four biological replicates (±SD), each from a pool of ≈980 seedlings. Statistical significance in pair-wise comparison was evaluated by Student's test, where  p≥0.01; * p≤0.001. (C). Chemical structure of 7-methylsulfonyl-heptyl-glucosinolate. (D) Structure of 7-methylsulfonyl-heptyl-isothiocyanate.

DETAILED DESCRIPTION OF THE INVENTION

Although methods and materials similar or equivalent to those described herein can be used in the practice or testing of the present invention, suitable methods and materials are described below. All publications, patent applications, patents, and other references mentioned herein are incorporated by reference in their entirety. The publications and applications discussed herein are provided solely for their disclosure prior to the filing date of the present application. Nothing herein is to be construed as an admission that the present invention is not entitled to antedate such publication by virtue of prior invention. In addition, the materials, methods, and examples are illustrative only and are not intended to be limiting.

In the case of conflict, the present specification, including definitions, will control.

Unless defined otherwise, all technical and scientific terms used herein have the same meaning as is commonly understood by one of skill in art to which the subject matter herein belongs. As used herein, the following definitions are supplied in order to facilitate the understanding of the present invention.

The term "comprise" is generally used in the sense of include, that is to say permitting the presence of one or more features or components.

As used in the specification and claims, the singular forms "a", "an" and "the" include plural references unless the context clearly dictates otherwise.

The presence of broadening words and phrases such as "one or more," "at least," "but not limited to" or other like phrases in some instances shall not be read to mean that the narrower case is intended or required in instances where such broadening phrases may be absent.

As used herein the terms "subject" or "patient" are well-recognized in the art, and, are used interchangeably herein to refer to a mammal, including dog, cat, rat, mouse, monkey, cow, horse, goat, sheep, pig, camel, and, most preferably, a human. In some embodiments, the subject is a subject in need of treatment or a subject with a disease or disorder. However, in other embodiments, the subject can be a normal subject. The term does not denote a particular age or sex. Thus, adult and new-born subjects, whether male or female, are intended to be covered.

The term "an effective amount" refers to an amount necessary to obtain a physiological effect. The physiological effect may be achieved by one application dose or by repeated applications. The dosage administered may, of course, vary depending upon known factors, such as the physiological characteristics of the particular composition; the age, health and weight of the subject; the nature and extent of the symptoms; the kind of concurrent treatment; the frequency of treatment; and the effect desired and can be adjusted by a person skilled in the art.

A "fungus" is a eukaryote that digests food externally and absorbs nutrients directly through its cell walls. Most fungi reproduce by spores and have a body (thallus) composed of microscopic tubular cells called hyphae. Fungi are heterotrophs and, like animals, obtain their carbon and energy from other organisms. Some fungi obtain their nutrients from a living host (plant or animal) and are called biotrophs; others obtain their nutrients from dead plants or animals and are called saprotrophs (saprophytes, saprobes). Some fungi infect a living host, but kill host cells in order to obtain their nutrients; these are called necrotrophs.

"Pathogenic fungi" also referred herein as "fungal pathogens" are fungi that cause disease in plants, humans or other organisms. Approximately 300 fungi are known to be pathogenic to humans. The study of fungi pathogenic to humans is called "medical mycology". Although fungi are eukaryotic, many pathogenic fungi are microorganisms. The study of fungi and other organisms pathogenic to plants is called plant pathology.

There are thousands of species of plant pathogenic fungi that collectively are responsible for 70% of all known plant diseases. Plant pathogenic fungi are parasites, but not all plant parasitic fungi are pathogens. Plant parasitic fungi obtain nutrients from a living plant host, but the plant host doesn't necessarily exhibit any symptoms. Plant pathogenic fungi are parasites and cause disease characterized by symptoms.

"Fungicides" are biocidal chemical compounds or biological organisms used to kill parasitic fungi or their spores (defined herein as fungitoxic). A fungistatic inhibits their growth. Fungi can cause serious damage in agriculture, resulting in critical losses of yield, quality, and profit. Fungicides are used both in agriculture and medicine to fight fungal infections in animals or humans. Chemicals used to control oomycetes, which are not fungi, are also referred to as fungicides, as oomycetes use the same mechanisms as fungi to infect plants. Fungicides can either be contact, translaminar or systemic. Contact fungicides are not taken up into the plant tissue and protect only the plant where the spray is deposited. Translaminar fungicides redistribute the fungicide from the upper, sprayed leaf surface to the lower, unsprayed surface. Systemic fungicides are taken up and redistributed through the xylem vessels. Few fungicides move to all parts of a plant. Some are locally systemic, and some move upwardly.

"Fungistatics" are anti-fungal agents that inhibit the growth of fungus (without killing the fungus). The term fungistatic may be used as both a noun and an adjective. Fungistatics have applications in agriculture, the food industry, the paint industry, and medicine.

Use of a composition comprising the combination of at least two compounds selected from general formula I:

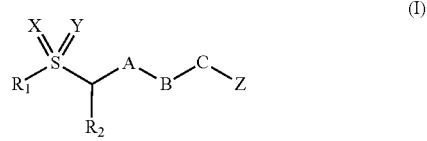

(I)

Wherein:
Z represents nitrile (—CN), thiocyanate (—SCN) or isothiocyanate (—N=C=S);
X, Y represent, independently of each other, a lone pair or O, with the proviso that at least one of the two X or Y is O;
$R_1$, $R_2$ represent, independently of each other, H, saturated linear, cyclic or branched $(C_1$-$C_6)$alkyl;
A, C represent, independently of each other, a covalent bond, saturated or unsaturated linear, cyclic, spirocyclic, bicyclic, polycyclic or branched $(C_1$-$C_8)$alkyl, $C_6$-aryl;
B represents, a covalent bond, saturated or unsaturated linear, cyclic, spirocyclic, bicyclic, polycyclic or branched $(C_1$-$C_8)$alkyl, $C_6$-aryl;
provided that at least one of A, B or C is different from a covalent bond, and characterized in that, the at least two combined compounds comprise:
1) at least one Z group representing isothiocyanate, and/or,
2) at least two different levels of oxidation of the sulphur atom, and/or,
3) at least a different length in the carbon chain residue -A-B-C-,
in the prevention or treatment of fungal pathogens in plants.

Preferably, aromatic rings can be substituted in ortho, meta and para;

cycloalkyl rings can be substituted at various positions, and cis or trans relative to the ring; and aliphatic and aromatic can be substituted by H, halogen or OMe groups.

Common oxidation states or "levels of oxidation" of sulphur range from −2 to +6. If sulphur has not been reduced nor oxidized; it possesses 6 valence electron. Of course, in sulphates, $SO_2$-4, and sulphites, $SO_2$-3, the sulphur atom assumes formal oxidation states of VI+, and IV+; in sulphides -II.

It is suggested that for the combination or mixture of the at least two compounds, the length in the carbon chain residue -A-B-C- is of importance. The combination may contain one short and one long chain, for example one containing a maximum of 6 linear carbon atoms and another one containing a minimum of 7 linear carbon atoms. However, in certain cases, the combination may contain at least two compounds with carbon chain residue -A-B-C- of the same length.

The composition of the invention to be effective in preventing or treating of fungal pathogens in plants should at least fulfil one of the above-cited criteria according to 1)-3). Combinations or mixtures of at least two compounds selected from general formula I and fulfilling criteria 1)-3) has shown an unexpected synergistic effect compared to single compounds tested alone.

It is usually accepted that "synergy" occurs when the combined action of two or more agents is greater than the sum of their individual effects. In other words, synergy is said to occur when the combined action of two or more agents is greater than could have been predicted based on the performance of the agents when used alone.

In particular, the composition of the invention is a mixture wherein at least one compound with Z representing nitrile and one compound with Z representing isothiocyanate.

Alternatively, the mixture corresponds to at least one compound with Z representing isothiocyanate and one compound with Z representing isothiocyanate.

Alternatively, the mixture corresponds to at least one compound with Z representing isothiocyanate and one compound with Z representing thiocyanate.

Alternatively, the mixture corresponds to at least one compound with Z representing thiocyanate and one compound with Z representing isothiocyanate.

Alternatively, the mixture corresponds to at least one compound with X representing a lone pair and Y representing an oxygen and at least one compound with X and Y representing an oxygen.

Alternatively the mixture corresponds to X and Y representing an oxygen.

Alternatively, the mixture corresponds to at least one compound with X representing a lone pair and Y representing an oxygen.

Alternatively the mixture of the invention where at least two compounds are selected with the same A/B/C formula where B represents a covalent bond and A and C represent independently of each other a saturated or unsaturated linear, cyclic, spirocyclic, bicyclic, polycyclic or branched (C1-C8) alkyl.

Preferably the mixture of the invention where at least two compounds are selected with different A/B/C formula where B represents a covalent bond and A and C represent independently of each other a saturated or unsaturated linear, cyclic, spirocyclic, bicyclic, polycyclic or branched (C1-C8) alkyl.

The term "lone pair" refers to a pair of valence electrons that are not shared with another atom and is sometimes called a non-bonding pair. Lone pairs are found in the outermost electron shell of atoms. They can be identified by using a Lewis structure. Electron pairs are therefore considered lone pairs if two electrons are paired but are not used in chemical bonding. Thus, the number of lone pair electrons plus the number of bonding electrons equals the total number of valence electrons around an atom. A single lone pair can be found with atoms in the nitrogen group such as nitrogen in ammonia, two lone pairs can be found with atoms in the chalcogen group such as oxygen in water and the halogens can carry three lone pairs such as in hydrogen chloride.

A "covalent bond", also called a molecular bond, is a chemical bond that involves the sharing of electron pairs between atoms. These electron pairs are known as shared pairs or bonding pairs, and the stable balance of attractive and repulsive forces between atoms, when they share electrons, is known as covalent bonding.

"Isothiocyanate" is the chemical group —N=C=S, formed by substituting the oxygen in the isocyanate group with a sulphur. Many natural isothiocyanates from plants are produced by enzymatic conversion of metabolites called glucosinolates. These natural isothiocyanates, such as allyl isothiocyanate, are also known as mustard oils. An artificial isothiocyanate, phenyl isothiocyanate, is used for amino acid sequencing in the Edman degradation.

The term "alkyl" as used herein refers to saturated and unsaturated aliphatic groups, including straight-chain alkyl groups, branched-chain alkyl groups, optionally substituted with one or several halogens. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer, e.g. from 1 to 6 carbons (defined as lower alkyl). Preferably, alkyls of the invention, have one to thirty, more preferably one to twenty, even more preferably one to twelve, more preferably one to eight, more preferably one to six, and most preferably from one to four carbon atoms and is linear or branched. The term "$C_1$-$C_6$ alkyl" represents a straight or branched alkyl chain having from one to six carbon atoms. Exemplary $C_1$-$C_6$ alkyl groups include methyl, ethyl, n-propyl, isopropyl, butyl, isobutyl, sec-butyl, t-butyl, pentyl, neo-pentyl, hexyl, isohexyl, and the like. Preferably, alkyl is a lower alkyl, such as n-butyl, sec-butyl, isobutyl, tert-butyl, n-propyl or isopropyl, ethyl or methyl.

The term "lower" in lower alkyl, lower alkoxy, lower alkenyl and lower alkynyl refers to a chain of up to 6 carbon atoms linked in a linear or branched fashion.

The term "cycloalkyl" represents a saturated or partially saturated, mono- or poly-carbocyclic ring, preferably having 5-14 ring carbon atoms. Exemplary cycloalkyls include monocyclic rings having from 3-7, preferably 3-6, carbon atoms, such as cyclopropyl, cyclobutyl, cyclopentyl, cyclohexyl, cycloheptyl and the like. An exemplary cycloalkyl is a $C_5$-$C_7$ cycloalkyl, which is a saturated hydrocarbon ring structure containing from five to seven carbon atoms.

The term "alkoxyl" represents —O-alkyl. An example of an alkoxyl is a $C_1$-$C_6$ alkoxyl, which represents a straight or branched alkyl chain having from one to six carbon atoms attached to an oxygen atom. Exemplary $C_1$-$C_6$ alkoxyl groups include methoxyl, ethoxyl, propoxyl, isopropoxyl, butoxyl, sec-butoxyl, t-butoxyl, pentoxyl, hexoxyl, and the like. $C_1$-$C_6$ alkoxyl includes within its definition a $C_1$-$C_4$ alkoxyl.

The term "aryl" as used herein refers to a carbocyclic or heterocyclic, aromatic, 5-14 membered monocyclic or polycyclic ring. Exemplary aryls include phenyl, naphthyl, anthryl, phenanthryl, thienyl, pyrrolyl, imidazolyl, pyrazolyl, furyl, isothiazolyl, furazanyl, isoxazolyl, thiazolyl, pyridyl, pyrazinyl, pyrimidinyl, pyridazinyl, triazinyl, benzo [b]thienyl, naphtho[2,3-b]thianthrenyl, isobenzofuranyl, chromenyl, xanthenyl, phenoxathienyl, indolizinyl, isoindolyl, indolyl, indazolyl, purinyl, isoquinolyl, quinolyl, phthalazinyl, naphthyridinyl, quinoxyalinyl, quinzolinyl, benzothiazolyl, benzimidazolyl, tetrahydroquinolinyl, cinnolinyl, pteridinyl, carbazolyl, beta-carbolinyl, phenanthridinyl, acridinyl, perimidinyl, phenanthrolinyl, phenazinyl, isothiazolyl, phenothiazinyl, and phenoxazinyl.

The term "halogen" represents chlorine, fluorine, bromine or iodine. The term "halo" represents chloro, fluoro, bromo or iodo.

The term "carbocycle" represents an aromatic or a saturated or a partially saturated 5-14 membered monocyclic or polycyclic ring, such as a 5- to 7-membered monocyclic or 7- to 10-membered bicyclic ring, wherein all the ring members are carbon atoms.

The term "polycyclic" refers to a polycyclic ring system, wherein at least two rings are connected together. As used herein, "polycyclic' refers to any ring system, which may be any degree of saturation, aromatic, aliphatic and optionally contain a heteroatom. The systems can be further classified according to the number of rings present (e.g., 2=bicyclic, 3=tricyclic, 4=tetracyclic, etc.) and the way the rings are connected together.

(1) Substituted rings systems: These ring systems have no common atoms. In these polycyclic systems, the smaller ring can be regarded as a substituent of the larger ring. By way of example only, biphenyl is a substituted polycyclic ring system.

(2) Spiro ring systems: Spiro ring systems share a single common atom. Hence the rings join at a single "point." The connecting atom is also called the spiroatom, most often a quaternary carbon ("spiro carbon"). By way of example, the spiro compound consisting of a cyclohexane ring and a cyclopentane ring is called spiro[4.5]decane.

(3) Fused ring systems: Fused ring systems share two common atoms in one common bond, hence the rings share one side. Examples of fused polycyclic ring systems include, but are not limited to, Naphthalene, Benzofuran, Indole, Benzothiophene, Quinoline and Anthracene.

(4) Bridged ring systems: Bridged ring systems share more than two common atoms, i.e., bridged ring systems contain interlocking rings. By way of example, Adamantane, Amantadine, Biperiden, Memantine, Methenamine, Rimantadine and Norbornane are all bridged ring systems.

The term "sulfonyl" represents —SO2-L5, wherein L5 is preferably alkyl, aryl, cycloalkyl, heterocycle or amino. The alkyl, aryl, cycloalkyl and heterocycle can all optionally be substituted. An example of a sulfonyl is a C1-C4 alkylsulfonyl, which is a straight or branched alkyl chain having from one to four carbon atoms attached to a sulfonyl moiety. Exemplary C1-C4 alkylsulfonyl groups include methylsulfonyl, ethylsulfonyl, propylsulfonyl, isopropyl sulfonyl, butylsulfonyl, sec-butylsulfonyl, t-butylsulfonyl, and the like.

As indicated above, many of the groups are optionally substituted. Examples of substituents for alkyl and aryl include mercapto, thioether, nitro ($NO_2$), amino, aryloxyl, halogen, hydroxyl, alkoxyl, and acyl, as well as aryl, cycloalkyl, and saturated and partially saturated heterocycles. Examples of substituents for heterocycle and cycloalkyl include those listed above for alkyl and aryl, as well as aryl and alkyl.

Exemplary substituted aryls include a phenyl or naphthyl ring substituted with one or more substituents, preferably one to three substituents, independently selected from halo, hydroxy, morpholino(C1-C4)alkoxy carbonyl, pyridyl (C1-C4)alkoxycarbonyl, halo (C1-C4)alkyl, C1-C4 alkyl, C1-C4 alkoxy, carboxy, C1-C4 alkoxycarbonyl, carbamoyl, N—(C1-C4)alkylcarbamoyl, amino, C1-C4 alkylamino, di(C1-C4)alkylamino or a group of the formula —(CH2)a-R<7> where a is 1, 2, 3, or 4, and R<7> is hydroxy, C1-C4 alkoxy, carboxy, C1-C4 alkoxycarbonyl, amino, carbamoyl, C1-C4 alkylamino or di(C1-C4)alkylamino.

Another substituted alkyl is halo(C1-C4)alkyl, which represents a straight or branched alkyl chain having from one to four carbon atoms with 1-3 halogen atoms attached to it. Exemplary halo(C1-C4)alkyl groups include chloromethyl, 2-bromoethyl, 1-chloroisopropyl, 3-fluoropropyl, 2,3-dibromobutyl, 3-chloroisobutyl, iodo-t-butyl, trifluoromethyl, and the like.

Another substituted alkyl is hydroxy(C1-C4)alkyl, which represents a straight or branched alkyl chain having from one to four carbon atoms with a hydroxy group attached to it. Exemplary hydroxy(C1-C4)alkyl groups include hydroxymethyl, 2-hydroxyethyl, 3-hydroxypropyl, 2-hydroxyisopropyl, 4-hydroxybutyl, and the like.

Yet another substituted alkyl is C1-C4 alkylthio(C1-C4) alkyl, which is a straight or branched C1-C4 alkyl group with a C1-C4 alkylthio group attached to it. Exemplary C1-C4 alkylthio(C1-C4)alkyl groups include methylthiomethyl, ethylthiomethyl, propylthiopropyl, sec-butylthiomethyl, and the like.

A cycloalkyl may be optionally substituted with 1, 2 or 3 substituents independently selected from halo, halo(C1-C4) alkyl, C1-C4 alkyl, C1-C4 alkoxy, carboxy, C1-C4 alkoxycarbonyl, carbamoyl, N—(C1-C4)alkylcarbamoyl, amino, C1-C4 alkylamino, di(C1-C4)alkylamino or a group having the structure —(CH2)a-R<7> where a is 1, 2, 3, or 4, and R<7> is hydroxy, C1-C4 alkoxy, carboxy, C1-C4 alkoxycarbonyl, amino, carbamoyl, C1-C4 alkylamino or di(C1-C4)alkylamino. Exemplary substituted cycloalkyl groups include 3-methylcyclopentyl, 4-ethoxycyclohexyl, 5-carboxycyclo-heptyl, 6-chlorocyclohexyl, and the like.

Double bonds in principle can have E- or Z-configuration. The compounds of this invention may therefore exist as isomeric mixtures or single isomers. If not specified both isomeric forms are intended. Where a compound of the invention contains one chiral centre, the compound can be provided as a single isomer (R or S) or as a mixture of isomers, for example a racemic mixture. Where a compound of the invention contains more than one chiral centre, the compound can be provided as an enantiomerically pure diastereoisomer or as a mixture of diastereoisomers.

In a particular embodiment, the invention provides the use of a composition comprising the combination of at least two isothiocyanate compounds, preferably said at least two isothiocyanate compounds have at least two different levels of oxidation of the sulphur atom, and/or at least a different length in the carbon chain residue -A-B-C-, preferably comprised between $C_3$ to $C_9$.

Preferably, the invention provides the use of a composition comprising the combination of at least two compounds selected from general formula I (as defined above):
wherein:
Z represents isothiocyanate (—N═C═S);
X, Y represent, independently of each other O;
R1, R2 represent, independently of each other, H, saturated linear or cyclic ($C_1$-$C_6$)alkyl;

A,C represent, independently of each other, a covalent bond, saturated or unsaturated linear or cyclic ($C_1$-$C_8$) alkyl, provided that at least one of A or C is different from a covalent bond;

B represents a covalent bond;

and wherein the length in the carbon chain residue -A-B-C- is from $C_3$ to $C_9$;

in the prevention of treatment of fungal pathogens in plants.

More preferably, the invention provides the use of a composition comprising the combination of the at least two compounds selected among the list comprising:

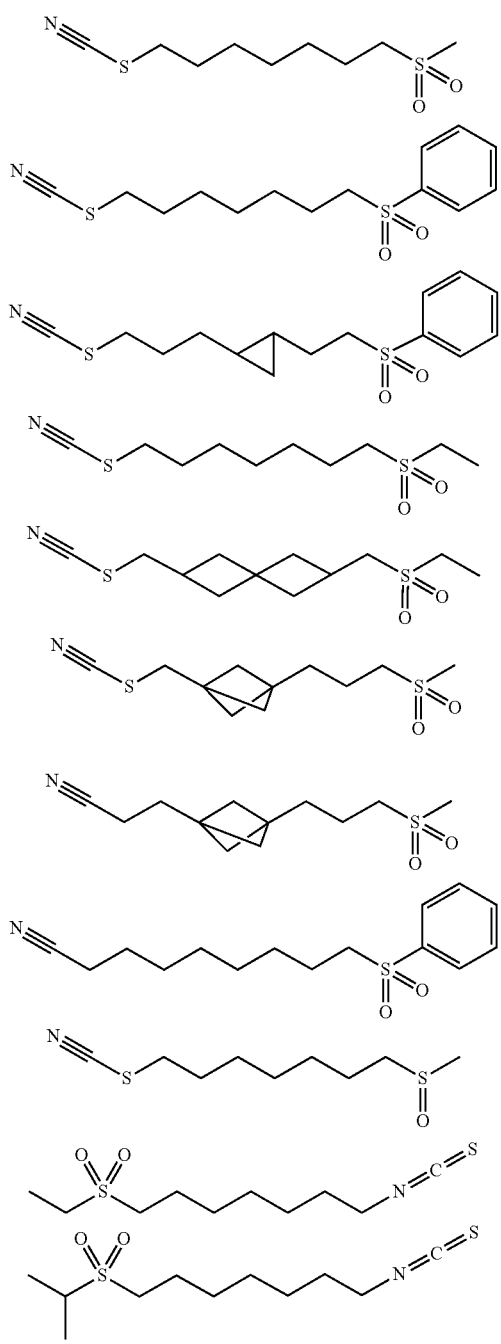

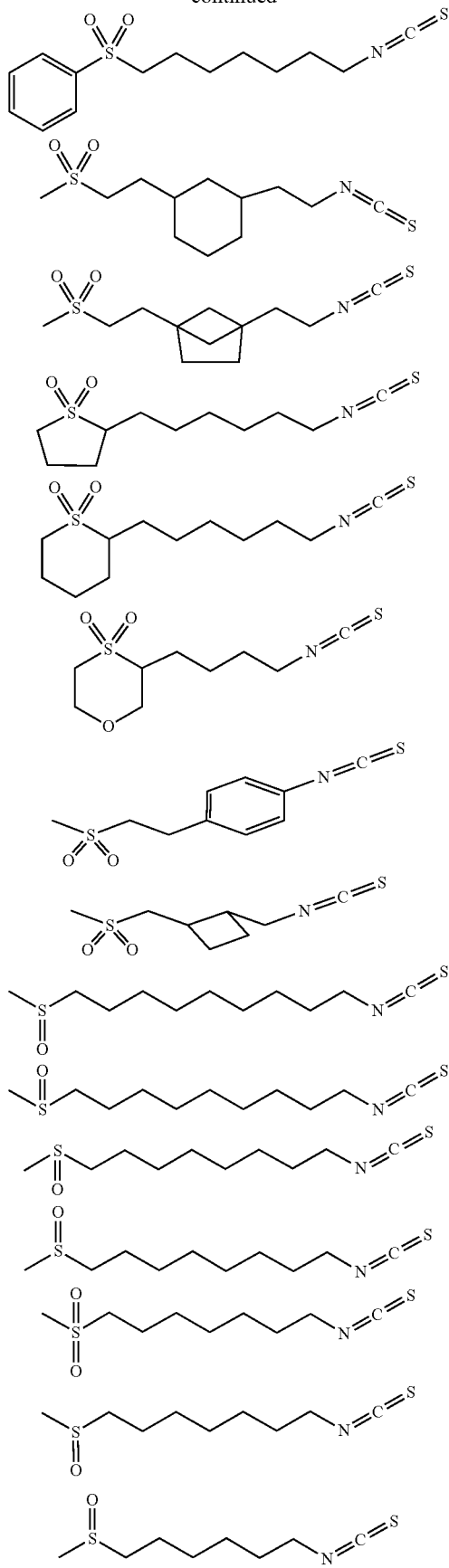

-continued

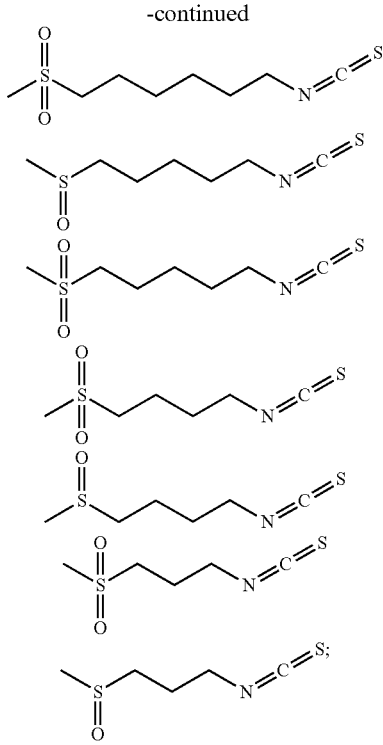

and wherein the at least two combined compounds comprise:
1) at least one Z group representing isothiocyanate, and/or,
2) at least two different levels of oxidation of the sulphur atom, and/or,
3) at least a different length in the carbon chain residue -A-B-C-,
4) and wherein the length in the carbon chain residue -A-B-C- is from C3 to C9;
in the prevention of treatment of fungal pathogens in plants.

Preferably, the at least two combined compounds to be used in the prevention or treatment of fungal pathogens in plants are selected from the group consisting of: 8MSOH/ 8MSOOH; 8ASOH/8ASOOH; 8ESOH/8ESOOH; 8CSOH/ 3MSOOH; 8CSOH/7MSOH; 8CSOH/3MSOH; 8MSOOH/ 6MSOH; 8MSOH/3MSOOH; 8MSOH/7MSOH; 8MSOH/ 6MSOH; 8CSOH/8MSOH; 8CSOH/3MSOOH; 8MSOH/ 9MSOOH; 8CSOH/7MSOH; 8ESOH/7MSOH; 8ESOH/ 3MSOH; 8MSOOH/7MSOH; 8MSOOH/9MSOH; 8MSOOH/6MSOH; 8CSOH/7MSOH; 8MSOOH/3MSOH; 8MSOOH/8MSOON or 8MSOOH/3MSOOH.

Even more preferably, the at least two combined compounds to be used in the prevention or treatment of fungal pathogens in plants is the mixture of 7 methylsulfonylheptyl and (E)-1-isothiocyanato-8-(methylsulfinyl)oct-2 or a mixture of 8 methylsulfonyloctyl isothiocyanate and 8 methylsulfinyloctyl isothiocyanate.

The identified compounds of the invention present several advantages, they reveal fungitoxic and/or fungistatic activity against environmental, plant, storage and medical fungal pathogens. Besides, the identified compounds of the invention do not reveal phytotoxicity, are stable in the light and can be freely applied on plants.

The composition used in the present invention has been shown to extend shelf-life by a minimum of one week for fruits, vegetables and cut flowers infected by fungal pathogens in storage facilities. Compounds used (i.e. mixture) were shown to be not toxic for insects and humans. The composition of the invention is easily applicable with a specific impact on the ripening perishable food and no extra installation cost is required. The composition of the invention is of interest to storage companies (i.e. reducing costs in packaging), the timber industry, gardeners and farmers.

Thus, the composition of the invention is to be used as a fungitoxic and/or as a fungistatic agent in plants. The composition of the invention to be used as a fungicide has shown a large efficacy in treating various plants or plant families (hosts). Indeed, the composition of the invention can be used in treating more than 1400 species of agronomical important crops or plants, including order of Solanales, Rosales, Vitales, Poales etc.

The composition of the invention may be used with any part of a plant during any part of its life cycle, including but not limited to seeds, seedlings, plant cells, plants, or flowers.

According to the invention, all plants and plant parts can be treated. By "plants" is meant all plants and plant populations such as desirable and undesirable wild plants, cultivars and plant varieties (whether or not protectable by plant variety or plant breeder's rights). Cultivars and plant varieties can be plants obtained by conventional propagation and breeding methods which can be assisted or supplemented by one or more biotechnological methods such as by use of double haploids, protoplast fusion, random and directed mutagenesis, molecular or genetic markers or by bioengineering and genetic engineering methods. By plant parts is meant all above ground and below ground parts and organs of plants such as shoot, leaf, blossom and root, whereby for example leaves, needles, stems, branches, blossoms, fruiting bodies, fruits and seed as well as roots, corms and rhizomes are listed. Crops and vegetative and generative propagating material, for example cuttings, corms, rhizomes, runners and seeds also belong to plant parts.

Among the plants that can be protected by the composition of the invention, mention may be made of major field crops like corn, soybean, cotton, Brassica oilseeds such as Brassica napus (e.g. canola), Brassica rapa, B. juncea (e.g. mustard) and Brassica carinata, rice, wheat, sugarbeet, sugarcane, oats, rye, barley, millet, triticale, flax, vine and various fruits and vegetables of various botanical taxa such as Rosaceae sp. (for instance pip fruit such as apples and pears, but also stone fruit such as apricots, cherries, almonds and peaches, berry fruits such as strawberries), Ribesioidae sp., Juglandaceae sp., Betulaceae sp., Anacardiaceae sp., Fagaceae sp., Moraceae sp., Oleaceae sp., Actinidaceae sp., Lauraceae sp., Musaceae sp. (for instance banana trees and plantings), Rubiaceae sp. (for instance coffee), Theaceae sp., Sterculiceae sp., Rutaceae sp. (for instance lemons, oranges and grapefruit); Solanaceae sp. (for instance tomatoes, potatoes, peppers, eggplant), Liliaceae sp., Compositiae sp. (for instance lettuce, artichoke and chicory—including root chicory, endive or common chicory), Umbelliferae sp. (for instance carrot, parsley, celery and celeriac), Cucurbitaceae sp. (for instance cucumber—including pickling cucumber, squash, watermelon, gourds and melons), Alliaceae sp. (for instance onions and leek), Cruciferae sp. (for instance white cabbage, red cabbage, broccoli, cauliflower, brussel sprouts, pak choi, kohlrabi, radish, horseradish, cress, Chinese cabbage), Leguminosae sp. (for instance peanuts, peas and beans beans—such as climbing beans and broad beans), Chenopodiaceae sp. (for instance mangold, spinach beet, spinach, beetroots), Malvaceae (for instance okra), Asparagaceae (for instance asparagus); horticultural and forest crops; ornamental plants and flowers including cut flowers; grass i.e. golf fields, turf, as well as genetically modified homologues of these crops.

active on at least 43 fungal pathogens (see list below), from 4 different phylum, 8 different classes and 14 different orders:

| Species | Phylum | Class | Order |
|---|---|---|---|
| Rhizoctonia solani | Basidiomycota | Agricomycetes | Cantharellales |
| Thamnidium elegans | Zygomyceta | Zygomycetes | Mucorales |
| Phytophthora cactorum | Oomycota | Oomycetes | Peronosporales |
| Phytophthora syringae | Oomycota | Oomycetes | Peronosporales |
| Phytophthora infestans | Oomycota | Oomycetes | Peronosporales |
| Phytophthora agathidicida strain 18407 | Oomycota | Oomycetes | Peronosporales |
| Phythium sp. | Oomycota | Oomycetes | Peronosporales |
| Plasmopara viticola | Oomycota | Oomycetes | Peronosporales |
| Aspergillus versicolor | Ascomycota | Eurotiomycetes | Eurotiales |
| Aspergillus pseudoglaucus | Ascomycota | Eurotiomycetes | Eurotiales |
| Aspergillus sp. | Ascomycota | Eurotiomycetes | Eurotiales |
| Penicillium vulpinum | Ascomycota | Eurotiomycetes | Eurotiales |
| Penicillium wortmannii | Ascomycota | Eurotiomycetes | Eurotiales |
| Trichophyton rubrum | Ascomycota | Eurotiomycetes | Onygenales |
| Lasiodiplodia theobromae | Ascomycota | Dothideomycetes | Botryosphaeriales |
| Guignardia bidwellii | Ascomycota | Dothideomycetes | Botryosphaeriales |
| Alternaria radicina | Ascomycota | Dothideomycetes | Pleosporales |
| Phoma exigua | Ascomycota | Dothideomycetes | Pleosporales |
| Phoma betae | Ascomycota | Dothideomycetes | Pleosporales |
| Helminthosporium solani | Ascomycota | Dothideomycetes | Pleosporales |
| Cladosporium langeronii | Ascomycota | Dothideomycetes | Capnodiales |
| Cladosporium haloterans | Ascomycota | Dothideomycetes | Capnodiales |
| Cladosporium sp. | Ascomycota | Dothideomycetes | Capnodiales |
| Fusarium verticillioides | Ascomycota | Sordariomycetes | Hypocreales |
| Fusarium gramineum | Ascomycota | Sordariomycetes | Hypocreales |
| Fusarium equiseti | Ascomycota | Sordariomycetes | Hypocreales |
| Fusarium culmorum | Ascomycota | Sordariomycetes | Hypocreales |
| Fusarium avenaceum | Ascomycota | Sordariomycetes | Hypocreales |
| Acremonium sp. | Ascomycota | Sordariomycetes | Hypocreales |
| Pyricularia oryzae | Ascomycota | Sordariomycetes | Magnaporthales |
| Scopulariopsis brevicaulis | Ascomycota | Sordariomycetes | Microascales |
| Scopulariopsis fusca | Ascomycota | Sordariomycetes | Microascales |
| Colletotrichum acutatum | Ascomycota | Sordariomycetes | Glomerellales |
| Colletotrichum coccodes | Ascomycota | Sordariomycetes | Glomerellales |
| Colletotrichum gloeosporioides | Ascomycota | Sordariomycetes | Glomerellales |
| Plectosphaerella cucumerina | Ascomycota | Sordariomycetes | Glomerellales |
| Monilinia laxa | Ascomycota | Leotiomycetes | Helotiales |
| Botrytis cinerea | Ascomycota | Leotiomycetes | Helotiales |
| Sclerotinia sclerotiorum | Ascomycota | Leotiomycetes | Helotiales |
| Gloeosporium album | Ascomycota | Leotiomycetes | Helotiales |
| Hymenoscyphus fraxineus | Ascomycota | Leotiomycetes | Helotiales |
| Geotrichum candidum | Ascomycota | Saccharomyces | Saccaromycetales |
| Pichia fermentans | Ascomycota | Saccharomyceses | Saccaromycetales |

For example, the composition of the present invention can be used for controlling common fungal diseases such as powdery mildew, rust, downy mildew, and anthracnose on field crops, fruit trees and vegetables.

In addition, the composition of the invention can be used for the treatment of resistant diseases, mainly for the control of wheat powdery mildew, rice blast, rice smut, melon powdery mildew, tomato powdery mildew, apple rust, watermelon Anthracnose and flower powdery mildew. Besides the composition has very good control effects against cucumber downy mildew, grape downy mildew, scab, anthrax, and spotted defoliation.

In a particular embodiment of the invention, the composition of the invention is to be used in the treatment or prevention of tree diseases, caused by fungal pathogens e.g. panama disease of banana, ash dieback.

Besides, the composition of the invention can be used directly in the field in plant cultures but also in vitro for example for implementation in plant cultures.

Surprisingly, the composition according to the present invention to be used as a fungicide has been found extremely In particular, the composition of the present invention has been shown effective against the plant fungal pathogens selected from the phylum comprising Basidiomycota, Zygomyceta, Oomycota or Ascomycota.

For example, the composition of the present invention has been shown particular effective against the plant fungal pathogens: *Botrytis cinerea, Colletotrichum graminicola, Fusarium oxysporum, Sclerotiana sclerotiorum, Verticillium dahlia, Mycospharella gramincola* and *Sphacelotheca reliana.*

In another embodiment, the composition of the invention (according to general formula I as defined above) can be used as an antimycotic in food or drink. The present invention also relates to a food and drink and an oral hygiene agent containing the above-mentioned antifungal agent.

In particular, the antifungal or antimycotic agent of the present invention can be added to foods or drinks to prevent food spoilage and fungus or contamination by pathogens.

In a particular embodiment of the invention, the composition of the invention can be advantageously used by food retailers for the shelf life extension of fruits and vegetables by preventing development of plant fungal pathogens. For example, the composition of the invention can extend the shelf life of vegetables, berries, fruits or cut flowers by at least one week.

Preferably, the amount added is in the range of 0.01 to 100 ppm based on the food.

More preferably from 1 to 50 ppm.

Examples of foods and beverages to which the antifungal agent of the present invention is to be blended include fish products, fish sausage, ham, fish meat sausage and ham, surimi products, fish and shellfish dried products, smoked products, salted fish, salted fish, shrimp Semi-solid marine products such as marinated cod roe and the like; livestock meat products such as ham, sausage, bacon and ground meat products; prepared foods such as salads, hamburgers, dumplings, boiled beans, Chinese cabbage, cucumbers, vegetables Pickles such as kimchee, sweet potato, tatami dish, and lotus rosemary; seasoning liquids such as sweet and soup; condiments such as miso and soy sauce; noodles such as raw or boiled buckwheat noodles, udon, pasta, various beverages such as fruit juices, carbonated drinks, tea, milk drinks, lactic acid bacteria beverages, coffee, cocoa, soy milk and the like; fruits and vegetables, Milk powder, fermented milk, butter, cheese, ice cream, dairy products such as cream, caramel, candy, chewing gums, jams, margarine and the like.

In a preferred embodiment, the antimycotic composition of the invention comprises the combination of at least two compounds selected from the group consisting of: 8MSOH/ 8MSOOH; 8ASOH/8ASOOH; 8ESOH/8ESOOH; 8CSOH/ 3MSOOH; 8CSOH/7MSOH; 8CSOH/3MSOH; 8MSOOH/ 6MSOH; 8MSOH/3MSOOH; 8MSOH/7MSOH; 8MSOH/ 6MSOH; 8CSOH/8MSOH; 8CSOH/3MSOOH; 8MSOH/ 9MSOOH; 8CSOH/7MSOH; 8ESOH/7MSOH; 8ESOH/ 3MSOH; 8MSOOH/7MSOH; 8MSOOH/9MSOH; 8MSOOH/6MSOH; 8CSOH/7MSOH; 8MSOOH/3MSOH; 8MSOOH/8MSOON or 8MSOOH/3MSOOH.

Even more preferably, the antimycotic composition of the invention comprises at least two combined compounds consisting in the mixture of 7 methylsulfonylheptyl and (E)-1-isothiocyanato-8-(methylsulfinyl)oct-2 or the mixture of 8 methylsulfonyloctyl isothiocyanate and 8 methylsulfinyloctyl isothiocyanate.

In yet another embodiment, the composition of the invention (according to general formula I as defined above) can be used as a disinfectant in oral hygiene or sanitary articles.

Preferably, the oral hygiene articles are selected among a dentifrice, a lozenge, a liquid or powdered mouthwash, a coating solution, a halitosis preventing agent, a chewing gum.

The dosage form of the oral hygiene agent to which the antimycotic agent of the present invention is blended may be any of a liquid preparation, a solid preparation, and a semisolid agent, and may be a dentifrice, a lozenge, a liquid or powdered mouthwash, Coating solution, halitosis preventing agent, chewing gum and the like.

Furthermore, the disinfectant of the present invention can be used in various products so-called antifungal goods (goods) such as kitchen utensils such as chopping boards, washing tools such as toothbrushes, stationery such as writing instruments, erasers and notes, clothing such as underwear products such as automobile interior items such as handles and seats; home appliances such as word processors and refrigerators; interior decoration materials such as tatami mats and wallpaper. That is, the antimycotic agent is kneaded into raw materials at the production stage of the above-mentioned commodity and mixed, or by adding an adjuvant such as a surfactant as necessary with this solvent to a product surface. Apply by applying or spraying as a spray. The liquid formulation or spray formulation can be applied as sanitary sheds, toilet seats, disinfectants for bathroom dails and mildewproofing agents. Furthermore, it can also be applied as a sanitary article such as a disinfecting cleaner or a wet tissue by impregnating the liquid formulated agent with a liquid-absorbent support such as paper or cloth.

In a preferred embodiment, the disinfectant composition of the invention comprises the combination of at least two compounds selected from the group consisting of: 8MSOH/ 8MSOOH; 8ASOH/8ASOOH; 8ESOH/8ESOOH; 8CSOH/ 3MSOOH; 8CSOH/7MSOH; 8CSOH/3MSOH; 8MSOOH/ 6MSOH; 8MSOH/3MSOOH; 8MSOH/7MSOH; 8MSOH/ 6MSOH; 8CSOH/8MSOH; 8CSOH/3MSOOH; 8MSOH/ 9MSOOH; 8CSOH/7MSOH; 8ESOH/7MSOH; 8ESOH/ 3MSOH; 8MSOOH/7MSOH; 8MSOOH/9MSOH; 8MSOOH/6MSOH; 8CSOH/7MSOH; 8MSOOH/3MSOH; 8MSOOH/8MSOON or 8MSOOH/3MSOOH.

Even more preferably, the disinfectant composition of the invention comprises at least two combined compounds consisting in the mixture of 7 methylsulfonylheptyl and (E)-1-isothiocyanato-8-(methylsulfinyl)oct-2 or the mixture of 8 methylsulfonyloctyl isothiocyanate and 8 methylsulfinyloctyl isothiocyanate.

Advantageously, the composition of the invention can also be used for the treatment or prevention of microbial infection selected from the list consisting of bacterial, fungal, yeast and/or viral infection.

In accordance with an embodiment of the invention, the bacterial infection comprises a gram positive or gram-negative infection.

In particular, the bacterial or yeast infection is a *Pseudomonas aeruginosa, Escherichia coli, S. aureus, S. epidermis, Klebsiellae pneumoniae, Acinetobacter baumannii, B. subtilis, E. aerogenes, C. freundii, Staphylococcus* spp, *Streptococcus* spp, *Enterococcus* spp, *Proteus* spp, *Candida* spp, *Apophysomyces* spp, *Aspergillus, Mucor* spp., *Porphymonas gingivalis, Prevotella intermedia, Treponema denticola, Tannerella forsythensis* or *Aggregatibacter actinomycetemcomitans* infections.

It is another object of the invention to provide a composition comprising the combination of at least two compounds selected from general formula I:

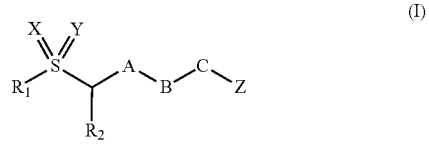

Wherein:
Z represents nitrile (—CN), thiocyanate (—SCN) or isothiocyanate (—N=C=S);
X, Y represent, independently of each other, a lone pair or O, with the proviso that at least one of the two X or Y is O;
$R_1$, $R_2$ represent, independently of each other, H, saturated linear, cyclic or branched ($C_1$-$C_6$)alkyl;
A, C represent, independently of each other, a covalent bond, saturated or unsaturated linear, cyclic, spirocyclic, bicyclic, polycyclic or branched ($C_1$-$C_8$)alkyl, $C_6$-aryl;
B represents, a covalent bond, saturated or unsaturated linear, cyclic, spirocyclic, bicyclic, polycyclic or branched ($C_1$-$C_8$)alkyl, $C_6$-aryl;

provided that at least one of A, B or C is different from a covalent bond, and characterized in that, the at least two combined compounds comprise:
1) at least one Z group representing isothiocyanate, and/or,
2) at least two different levels of oxidation of the sulphur atom, and/or,
3) at least a different length in the carbon chain residue -A-B-C-, for use in a method for preventing or treating mycosis in human or animal patients.

Preferably, the composition is a pharmaceutical composition.

The pharmaceutical composition according to the invention can be used for the preparation of a medicament useful to curatively or preventively treat human or animal fungal diseases such as, for example, mycoses, chytrid infections (Bd; Bs), dermatoses, trichophyton diseases and candidiases or diseases caused by *Aspergillus* spp., for example *Aspergillus fumigatus*.

In an embodiment of the invention, the mycosis is due to *Candida albicans* or *Trichophyton rubrum* infections.

In particular, the antifungal agent of the present invention has an excellent antimicrobial activity against *Candida albicans*, which is regarded as one of causative yeast of denture stomatitis, so if it is blended into an oral hygiene agent according to a conventional method, *Candida*'s infection can be effectively prevented and treated.

Besides, the antifungal agent of the present invention can be used in combination with other antimicrobial agents such as alcohol, spice ingredients such as sage and rosemary; organic acids such as citric acid, lactic acid, acetic acid and the like.

In a preferred embodiment, the antifungal agent of the invention for preventing or treating mycosis in human or animal patients comprises the combination of at least two compounds selected from the group consisting of: 8MSOH/8MSOOH; 8ASOH/8ASOOH; 8ESOH/8ESOOH; 8CSOH/3MSOOH; 8CSOH/7MSOH; 8CSOH/3MSOH; 8MSOOH/6MSOH; 8MSOH/3MSOOH; 8MSOH/7MSOH; 8MSOH/6MSOH; 8CSOH/8MSOH; 8CSOH/3MSOOH; 8MSOH/9MSOOH; 8CSOH/7MSOH; 8ESOH/7MSOH; 8ESOH/3MSOH; 8MSOOH/7MSOH; 8MSOOH/9MSOH; 8MSOOH/6MSOH; 8CSOH/7MSOH; 8MSOOH/3MSOH; 8MSOOH/8MSOON or 8MSOOH/3MSOOH.

More preferably, the at least two combined compounds to be used in the method for preventing or treating mycosis in human or animal patients is the mixture of 7 methylsulfonylheptyl and (E)-1-isothiocyanato-8-(methylsulfinyl)oct-2 or a mixture of 8 methylsulfonyloctyl isothiocyanate and 8 methylsulfinyloctyl isothiocyanate.

It is yet another object of the invention to provide a fungicide composition comprising the combination of at least two compounds selected from general formula I:

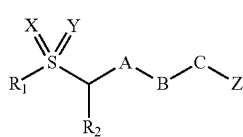

(I)

Wherein:
Z represents nitrile (—CN), thiocyanate (—SCN) or isothiocyanate (—N=C=S);

X, Y represent, independently of each other, a lone pair or O, with the proviso that at least one of the two X or Y is O;
$R_1$, $R_2$ represent, independently of each other, H, saturated linear, cyclic or branched ($C_1$-$C_6$)alkyl;
A, C represent, independently of each other, a covalent bond, saturated or unsaturated linear, cyclic, spirocyclic, bicyclic, polycyclic or branched ($C_1$-$C_8$)alkyl, $C_6$-aryl;
B represents, a covalent bond, saturated or unsaturated linear, cyclic, spirocyclic, bicyclic, polycyclic or branched ($C_1$-$C_8$)alkyl, $C_6$-aryl;
provided that at least one of A, B or C is different from a covalent bond,
and characterized in that, the at least two combined compounds comprise:
1) at least one Z group representing isothiocyanate, and/or,
2) at least two different levels of oxidation of the sulphur atom, and/or,
3) at least a different length in the carbon chain residue -A-B-C-.

Preferably, the fungicide composition comprises the combination of at least two compounds selected from general formula I, wherein:
Z represents isothiocyanate (—N=C=S);
X, Y represent, independently of each other O;
$R_1$, $R_2$ represent, independently of each other, H, saturated linear or cyclic ($C_1$-$C_6$)alkyl;
A, C represent, independently of each other, a covalent bond, saturated or unsaturated linear or cyclic ($C_1$-$C_8$) alkyl, provided that at least one of A or C is different from a covalent bond;
B represents a covalent bond;
and wherein the length in the carbon chain residue -A-B-C- is from $C_3$ to $C_9$.

In a particular embodiment, the fungicide composition of the invention comprises the combination of at least two isothiocyanate compounds, preferably said at least two isothiocyanate compounds have at least two different levels of oxidation of the sulphur atom, and/or at least a different length in the carbon chain residue -A-B-C-, preferably comprised between $C_3$ to $C_9$.

More preferably, the fungicide composition of the invention comprises the combination of the at least two compounds selected among the list comprising:

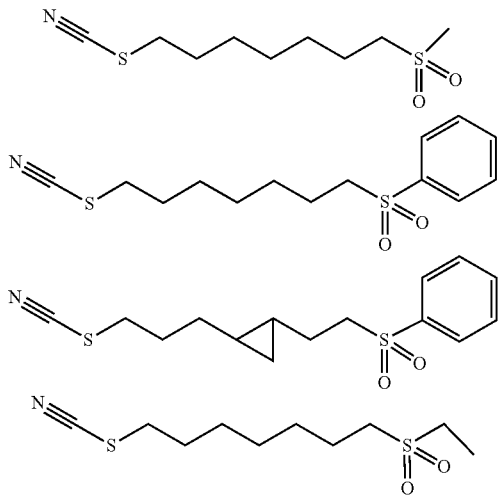

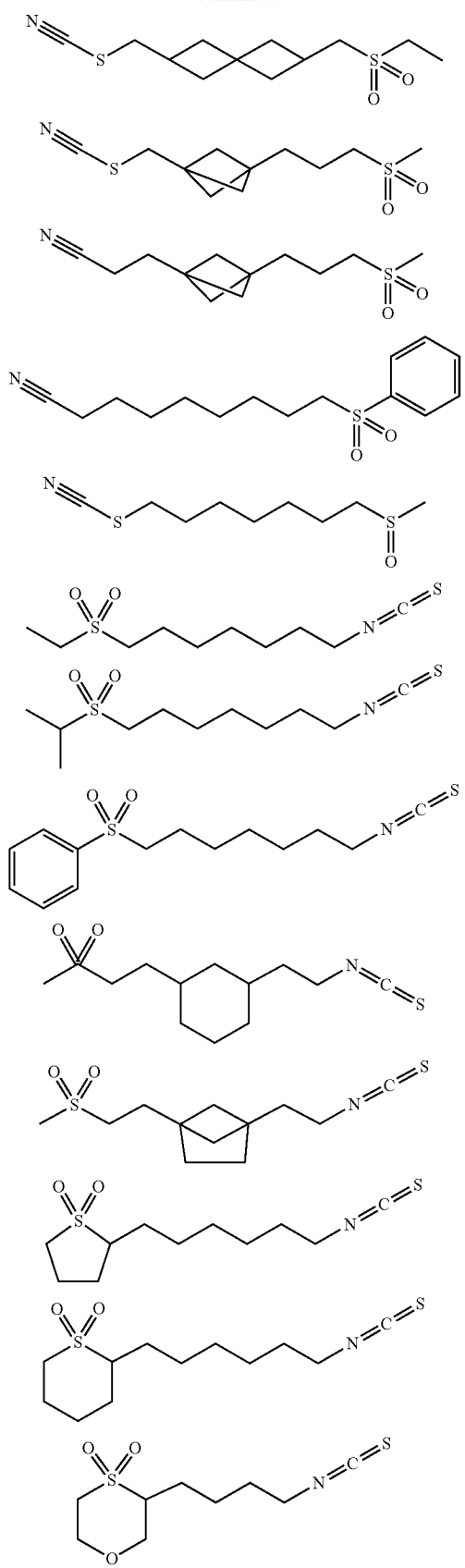
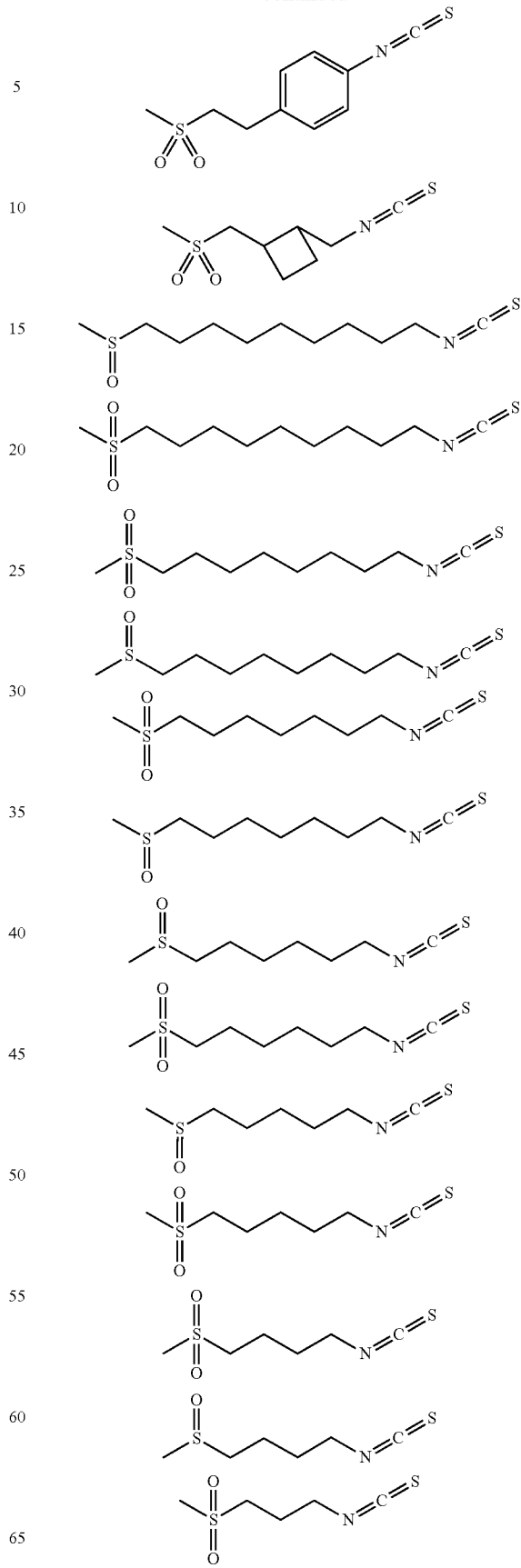

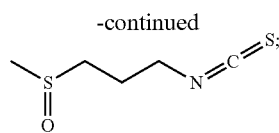

wherein the at least two combined compounds comprise:
1) at least one Z group representing isothiocyanate, and/or,
2) at least two different levels of oxidation of the sulphur atom, and/or,
3) at least a different length in the carbon chain residue -A-B-C-, and wherein the length in the carbon chain residue -A-B-C- is from $C_3$ to $C_9$.

Preferably, the at least two combined compounds of the fungicide composition according to the invention are selected from the group consisting of: 8MSOH/8MSOOH; 8ASOH/8ASOOH; 8ESOH/8ESOOH; 8CSOH/3MSOOH; 8CSOH/7MSOH; 8CSOH/3MSOH; 8MSOOH/6MSOH; 8MSOH/3MSOOH; 8MSOH/7MSOH; 8MSOH/6MSOH; 8CSOH/8MSOH; 8CSOH/3MSOOH; 8MSOH/9MSOOH; 8CSOH/7MSOH; 8ESOH/7MSOH; 8ESOH/3MSOH; 8MSOOH/7MSOH; 8MSOOH/9MSOH; 8MSOOH/6MSOH; 8CSOH/7MSOH; 8MSOOH/3MSOH; 8MSOOH/8MSOON or 8MSOOH/3MSOOH.

Even more preferably, the at least two combined compounds of the fungicide composition is a mixture of 7 methylsulfonylheptyl and (E)-1-isothiocyanato-8-(methylsulfinyl)oct-2 or a mixture of 8 methylsulfonyloctyl isothiocyanate and 8 methylsulfinyloctyl isothiocyanate.

In particular, the fungicide composition of the present invention has been shown effective against the plant fungal pathogens selected from the phylum comprising: Basidiomycota, Zygomyceta, Oomycota, Ascomycota.

For example, the fungicide composition of the present invention has been shown particularly effective against the plant fungal pathogens: *Botrytis cinerea, Colletotrichum graminicola, Fusarium oxysporum, Sclerotiana sclerotiorum, Verticillium dahlia, Mycospharella gramincola* and *Sphacelotheca reliana.*

In an embodiment of the invention, the fungicide composition of the invention is applied in combination with acceptable carriers or diluents, i.e. in a spray.

The fungicide composition of the invention will often be concentrated formulations that can be diluted in water, or another liquid, for application. In certain embodiments, the fungicide composition can also be formulated into particles or granular formulations that are sprayed or applied without further treatment.

Preferably, carriers or diluents to be used in the present invention are phytologically-acceptable.

As used herein, the term "phytologically-acceptable" formulations refers to compositions, diluents, excipients, and/or carriers that are generally applicable for use with any part of a plant during any part of its life cycle, including but not limited to seeds, seedlings, plant cells, plants, or flowers. The formulations can be prepared according to procedures, methods and formulas that are conventional in the agricultural arts. Following the teachings of the present invention, the person skilled in the agricultural and/or chemical arts can readily prepare a desired composition. Most commonly, the fungicide composition of the present invention can be formulated to be stored, and/or applied, as aqueous or non-aqueous suspensions or emulsions prepared neat or from concentrated formulations of the compositions. Water-soluble, water-suspendable or emulsifiable formulations can also be converted into or formulated as solids (e.g., wettable powders), which can then be diluted into a final formulation. In certain formulations, the fungicide compositions of the present invention can also be provided in growth media, e.g., in vitro media for growth of plant or other types of cells, in laboratory plant growth media, in soil, or for spraying on seeds, seedlings, roots, stems, stalks, leaves, flowers or the entire plant.

These phytologically-acceptable formulations are produced in a known manner, for example by mixing the fungicide composition of the invention with extenders, that is liquid solvents, liquefied gases under pressure, and/or solid carriers, optionally with the use of surfactants, that is emulsifiers and/or dispersants, and/or foam formers. If the extender used is water, it is also possible to use, for example, organic solvents as auxiliary solvents. Essentially, suitable liquid solvents include: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water. Liquefied gaseous extenders or carriers are to be understood as meaning liquids which are gaseous at ambient temperature and under atmospheric pressure, for example aerosol propellants such as butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkyl-sulphonates, alkyl sulphates, arylsulphonates, or else protein hydrolysates. Suitable dispersants are: for example lignin-sulphite waste liquors and methylcellulose.

The fungicide composition according to the invention can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra-low volume (ULV) liquid, ultra-low volume (ULV) suspension, water dispersible granules or tablets, water dispersible powder for slurry treatment, water soluble granules or tablets, water soluble powder for seed treatment and wettable powder. These compositions include not only compositions that are ready to be applied to the plant or seed to be treated by means of a suitable device, such as a spraying or dusting device, but also concentrated commercial compositions that must be diluted before application to the crop.

In a preferred embodiment of the invention, the composition can be specifically applied on fruits and vegetables in storage facilities with an ultrasonic fogger. The ultrasonic fogger is a device that is using ultrasonic sound waves to break water into very small droplets (<10 um) and sprays it into the air as a dense cold fog (i.e. not resulting from boiling water). Examples of ultrasonic foggers and systems are i.e. described in the following U.S. Patents: U.S. Pat. Nos. 4,042,016; 4,058,253; 4,118,945; 4,564,375; 4,667,465; 4,702,074; 4,731,990; 4,731,998; 4,773,846; 5,454,518; 6,854,661. Usually an ultrasonic fogger includes: a generally cylindrical body having an axial bore with an outlet at a front face of the body; a gas supply and a liquid supply coupled to the bore; at least a portion of the front face having a curved convex contour, the front face having a flat central annular region surrounding the outlet of the bore; and a resonator spaced from and opposing the outlet end of the bore. Such devices are commonly used to control humidity level in greenhouses, to deliver nutrients to plant in aeroponic cultures or to create optimal humidity levels in houses.

Applicants demonstrated that this technique can be used to apply products used for the extension of fruits and vegetables freshness in storage facilities e.g. natural fungicides. This technology, permits to efficiently treat fruits and vegetables that are not accessible to the treatments applied by spray or other applications, due to their packaging (i.e. it cannot be easily sprayed directly because fruits and vegetables are stored e.g. in container or because spraying might damage the fruits and vegetables).

Interestingly, Applicants performed efficacy trials on fruits and vegetables in a storage facility of 30 $m^3$ using an industrial MHS15 Ultrasonic Humidifiers (http://www-.mainlandmart.com/humidify.html), generating 15 kg of fog/hour made of droplets of a size comprised between 1-10 μm with average 5 micron. The composition of the invention, represented by powder was added into water container of the fogger in a dosage of 400-600 μM, depending on the tested plant species. Powder was dissolved in the water and applied on the fruits in a form of cold vapor. Applicants, have confirmed equal distribution of the product on all treated crops and easy access to the inaccessible previously parts of the package.

The fungicide composition according to the invention can also be mixed with one or more insecticides, pesticides, attractants, sterilants, bactericides, acaricides, nematicides, other fungicides, growth regulators, herbicides, fertilizers, safeners, semiochemicals, flavour exhauster agents or other compounds with biological activity. The mixtures thus obtained have normally a broadened spectrum of activity. The mixtures with other fungicide compounds are particularly advantageous.

The fungicide composition according to the invention comprising a mixture with a bactericide compound can also be particularly advantageous. Examples of suitable bactericide mixing partners can be selected in the following list: bronopol, dichlorophen, nitrapyrin, nickel dimethyldithiocarbamate, kasugamycin, octhilinone, furancarboxylic acid, oxytetracycline, probenazole, streptomycin, tecloftalam, copper sulfate and other copper preparations.

The dose of the fungicide composition usually applied in the treatment according to the invention is generally and advantageously from 10 to 800 g/ha, preferably from 50 to 300 g/ha for applications in foliar treatment. The dose of fungicide composition applied is generally and advantageously from 2 to 200 g per 100 kg of seed, preferably from 3 to 150 g per 100 kg of seed in the case of seed treatment.

It is clearly understood that the doses indicated herein are given as illustrative examples of the treatment method according to the invention. A person skilled in the art will know how to adapt the application doses, notably according to the nature of the plant or crop to be treated. Glucosinolates are sulfur- and nitrogen-containing secondary metabolites that are present in the order of Capparales, which includes agronomically important Brassicaceae family. Approximately 200 glucosinolates were described, so far. All of them can be subdivided on three major groups based on their amino acids precursors: aliphatic, indolic and aromatic glucosinolates. The role of these metabolites in plants is not fully understood, however they were shown to be involved in defence responses against herbivores, some fungal (Schreiner and Koide, 1993) and bacterial pathogens (Dufour et al., 2015). Glucosinolates are not active in intact form, however, during tissue damage e.g. herbivore attack, they are broken down to three major bioactive compounds: nitriles, thiocyanates, and isothiocyanates by myrosinase enzyme. All three active compounds were shown to be toxic to a large group of plant pathogens (Lambrix et al., 2001). In this study, Applicants had surprisingly revealed a new role of aliphatic glucosinolates, specifically methylsulfonyl and methylsulfinyl straight alkyl chain compounds ($CH_3S(O)_2(CH_2)_n$) in toxicity to fungal pathogens.

For this purpose, Applicants selected *Arabidopsis thaliana* mutants affected in the cuticle composition and performed fungi toxicity assays using *Botrytis cinerea* —a second agronomically important fungal pathogen, for which no efficient organic treatment exists to date. Based on the obtained results, the following mutants revealed strong resistance to *B. cinerea*: fatty acid desaturase mutants (fad2; fad3-2 fad7-2 fad8), a cytochromes P450 belonging to CYP77 family/defensive in cuticle ridges (cyp77 dcr), glycerol-3-phosphate acyltransferase/permeable cuticle 1 (gpat6 pec1) and glycerol-3-phosphate acyltransferase (gpat4 gpat8) double knockout mutants. All of selected mutants displayed a strong resistance against *B. cinerea* either only at the cotyledon stage (fad mutants) or at both seedlings and adult stages (cyp77 dcr; gpat6 pec1; gpat4 gpat8 double mutants). To understand what leads to fungal resistance in these plants, diverse approaches were used e.g. molecular biology, microscopy and biochemistry. Testing for the currently known mechanisms that are involved in *B. cinerea* resistance, i.e. hormonal changes, higher ROS levels and surface modification, could not fully explain *B. cinerea* resistance. These results lead Applicants to the use of surface metabolomics approach to identify potential antifungal compounds on the plant surface. With the help of this technic, Applicants were able to identify 2 compounds strongly abundant on the surface of different cuticle mutants: 7-methylsulfonyl-heptyl glucosinolate (on the cotyledons of fad2 mutants), to Applicant's knowledge not identified earlier in *Arabidopsis* plants, and 8-methylsulfonyl-octyl glucosinolate (on the cotyledons of fad3-2 fad7-2fad8 and leaves of gpat6 pec1 mutants). Focusing on the general structure of the first identified compounds led Applicants to the identification of 2 major groups of aliphatic glucosinolates and their mixtures strongly involved in fungal resistance.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended Claims, and all changes, which come within the meaning and range of equivalency, are intended to be embraced therein.

The foregoing description will be more fully understood with reference to the following Examples. Such Examples, are, however, exemplary of methods of practising the present invention and are not intended to limit the scope of the invention.

EXAMPLES

Materials and Methods

*Arabidopsis thaliana* accession Columbia-0 (Col-0) was used as the wild type (WT) plant. The following alleles in Col-0 background were received from the *Arabidopsis* Biological Resource Centre (ABRC): fad2-1 (CS8041), fad2-3 (SK18137), the fad2-1 fad6 and fad2-3 fad6 were obtained by crossing of the single mutants in this work. Double mutant gpat4 gpat8 was kindly provided by Frédéric Beisson, fad3-2 fad7-2 fad8 seeds were offered by John Browse, cyp77 der and gpat6 pec1 double mutants were kindly provided by Dr. Christiane Nawrath. Before planting seeds were stratified for 2 days at 40° C. and then grown at 21° C. under 100 µE m-2 s-1 of light with photoperiods depending on the application (experiments with seedlings: 14 h light, 10 h dark (long day); on soil for seed propagation: 24 h light, continuous day).

Seedlings used for experiments were grown on half-strength Murashige and Skoog solid media (0.5*MS, 2.15 g/L, pH 5.7; Duchefa Biochemie, Haarlem, The Nederlands) supplemented with 0.5 g/L of MES hydrate (Sigma, Buchs, Switzerland) and 0.7% plant agar (Sigma, Buchs, Switzerland). After stratification seeds were placed on the nylon mesh (200 µm pore size; product number AH03444, Lanz-Anliker AG, Rohrbach, Switzerland) to provide solid support for uniform seedling germination and growth. All the chemicals were obtained from Sigma-Aldrich unless indicated.

In Vivo Fungal Bioassay with *B. cinerea*

Two strains of *B. cinerea* were used in this work: BMM and B05.10 provided by Dr.

Christiane Nawrath and Prof. Michael Hahn, respectively. The fungus was grown on potato dextrose agar (PDA) for 10 days. Conidia were filtered and diluted to 5*105 spores/µl in ½ strength potato dextrose broth (PDB). 2 µl of this suspension were applied on 7-day-old *Arabidopsis* cotyledons grown in petri dishes. Infected seedlings were incubated for 48 h in long day conditions.

In Vitro Fungal Bioassay.

Methylsulfonyl and methylsulfinyl nitrile and thiocyanates were obtained from SpiroChem (Basel, Switzerland), methylsulfonyl and methylsulfinyl isothiocyanates from SpiroChem and LKT LABS (Minnesota, United States of America). All the obtained compounds were dissolved in dimethyl sulfoxide (DMSO). Fungal strains used during for in vitro fungal bioassay were obtained from the mycotheca of Agroscope (www.mycoscone.bcis.ch).

Pure cultures of different species of plant fungal pathogens were inoculated on PDA implemented with by-products of aliphatic glucosinolates that were preliminary dissolved to various concentration (e.g. 10, 100, 250, 400, 550, 700, 850, 1100, 1400 µM) in PDB and placed on the 24 well plates (VWR International, Dietikon, Switzerland). Controls were treated in similar way with DMSO alone. 2 mm agar plug (Dufour et al. 2015) of a fungal pre-culture were placed on each well, 3 biological replicates were used for each concentration. Plates were incubated for the period of one week in the phytotron (80% relative humidity, constant temperature of 23° C., under alternating 16 h day and 8 h night cycles). Mycelia growth was measured after 7 days using ImageJ (http://imagej.net/Welcome), $EC_{50}$ was evaluated as described in Schnee et al., 2013.

Metabolomics Analysis

The ultra-high performance liquid chromatography-quadrupole time-of-flight mass spectrometry (UPLC/QTOF-MS) on an Acquity ultra-performance liquid chromatography (UPLC) to a Synapt G2 quadrupole time-of-flight mass spectrometer mass spectrometer (QTOF; Waters) was used to carry out this experiment. An Acquity UPLC ethylene bridge hybrid (BEH) C18 column (50×2.1 mm, 1.7 m; Waters) was employed at a flow rate of 400 µL/min and maintained at a temperature of 25° C. The following gradient was used with 0.05% formic acid in water as mobile phase A and 0.05% formic acid in acetonitrile as mobile phase B: 0.0-7.0 min 2-100% B, 7.0-9.0 min 100% B, 9.0-11.0 min 2% B. The injection volume was 2.5 µL. The QTOF was operated in electrospray negative mode using the $MS^E$ (simultaneous acquisition of full scan and all fragment ions) mode. Mass spectrometric parameters were as follows: mass range 85-1200 Da, scan time 0.2 s, source temperature 120° C., capillary voltage −2.0 kV, cone voltage −25V, extraction cone −4.5 V, de-solvation gas flow and temperature 800 L/h and 400° C., respectively, cone gas flow 20 L/h, collision energy 4 eV (low energy acquisition function) and 10-35 eV (high energy acquisition function), collision gas (argon) 7×10-3 mbars. A 400 ng/mL solution of the synthetic peptide leucine-enkepaline in water: acetonitrile: formic acid (50:50:0.1) was infused constantly into the mass spectrometer as internal reference to ensure accurate mass measurements. Data were recorded by Masslynx v.4.1 (Waters). Marker detection was performed using Markerlynx XS (Waters) with the following parameters: initial and final retention time 0.0 and 9.0 min, mass range 85-1200 Da, mass window 0.02 Da, retention time window 0.06 min, intensity threshold 500 counts, automatic peak width and peak-to-peak baseline noise calculation, de-isotoping function applied. Data were mean—centered and Pareto—scaled before applying principal component analysis. Markers of interest were tentatively identified based on their molecular formula determination and fragments obtained by collision-induced dissociation.

Example 1

The 7-methylsulfonyl-heptyl glucosinolate was identified on the surface of fatty acid desaturase 2 (fad2-3) *Arabidopsis thaliana* mutant that revealed strong resistance to necrotrophic fungal pathogen *Botrytis cinerea* at the cotyledon stage (FIG. 1). Confirmation of antifungal activity of 7-methylsulfonyl-heptyl isothiocyanate (7MSOOH, the only commercially available by-product of 7-methylsulfonyl-heptyl glucosinolate) against *B. cinerea* and other fungal pathogens was performed in vitro by direct application of isothiocyanate in potato dextrose agar in different dosages. Obtained results reveled no fungitoxic activity of this compound against *Botrytis cinerea* in the dose range between 10 and 1500 µM. Higher dosages were not applied, due to the potential toxic effect of this compound. However, performance of bioassay on other fungal pathogens allowed to identify that 7-methylsulfonyl-heptyl isothiocyanate is fungitoxic to some fungal species, as shown in Table 1.

TABLE 1

Antifungal properties of 7-methylsulfonyl-heptyl isothiocyanate revealed upon in vitro antifungal assay.

| # | Fungal spp. | Host organism | ED50 (μM) |
|---|---|---|---|
| 1 | Septoria tritici | Wheat | 350 |
| 2 | Colletotrichum dematium | Various plant species | 650 |
| 3 | Serpula lacrymans | Wood | 150 |
| 4 | Hemenoscyphus fraxineus | Ash trees | 770 |

Conclusion: 7-methylsulfonyl-heptyl isothiocyanate reveals a narrow range of fungitoxic activity on a few plant fungal pathogens and shows to be non-active on broadly spread plant fungal pathogens as *Botrytis cinerea* (Grey mold) or *Fusarium oxysporum*. However, Applicants have surprisingly shown that the combination of glucosinolates' by-products leads to strong fungitoxic activity on a large number of agronomical important fungal pathogens (43 species, see table on pages 23-24 for the list of species).

Example 2

Investigation of other natural by-products of glucosinolates and their combinations led Applicants to identify highly efficient antifungal mixtures of compounds. Applicants used the effective dose that produces a quantitative effect in 95% of the population (ED95) at the maximal concentration of 1500 μM to investigate the fungitoxic activity of analyzed compounds. Applicants have chosen two most broadly spread plant fungal pathogens to perform toxicity assay: *Botrytis cinerea* (pathogen of 1400 plant species) and *Fusarium oxysporum* (pathogen of a large number of plant species e.g. tomato, bananas). Selection of such fungal pathogens was caused by the absence of any efficient organic treatment (less than 60% of efficiency) on the market that creates a need for identifying new efficient products which can be used by farmers with no risk for their health and also for the environment.

Initially, applicants had tested single molecules of 8-methylsulfonyl-octyl- (8MSOOH) and 8-methylsulfinyl-octyl- (8MSOH) isothiocyanates that revealed no fungitoxic effect on *Botrytis cinerea* and *Fusarium oxysporum*. However, once 8-methylsulfonyl-octyl- (8MSOOH) and 8-methylsulfinyl-octyl-isothiocyanate (8MSOH) are combined together they become highly toxic to *B. cinerea* (1400 μM) and *F. oxysporum* (923.64 μM).

Surprisingly, toxicity assay with 8-methylsulfonyl-octyl-nitrile (8MSOON) and 8-methylsulfonyl-octyl-isothiocyanate (8MSOOH) revealed different effect on two fungal species. Combination of nitrile and isothiocyanates was toxic to *B. cinerea* in the dosage of 850 μM (lower than the combination of the two isothiocyanates). However, this combination had mild effect on the development on *F. oxysporum*. For this fungal pathogen, the fungitoxic effect was obtained with the combination of 8MSOOH+8MSOH, with an EC95 of 923.64 μM.

Combination of three molecules together (isothiocyanates and nitriles) did not lead to an increase in the fungitoxic activities of these molecules and stayed at the same level than the one with the most efficient combination of the 2 molecules. Results of single and combinations of molecules are presented in Table 2.

TABLE 2

Fungitoxic activity of diverse by-products of glucosinolate (combined and single molecules) against *Botrytis cinerea* and *Fusarium oxysporum*.

| $ED_{95}$ | Botrytis cinerea | F. oxysporum |
|---|---|---|
| 8MSOH | <1500 | <1500 |
| 8MSOON | <1500 | <1500 |
| 8MSOOH | <1500 | <1500 |
| 8MSOH + 8MSOON | <1500 | <1500 |
| 8MSOOH + 8MSOON | 850 | <1500 |
| 8MSOOH + 8MSOH | 1400 | 923.64 |
| 8MSOOH + 8MSOON + 8MSOH | 850 | 1125.08 |

Conclusion: By-products of methylsulfonyl and methylsulfinyl glucosinolates used separately reveal no fungitoxic activity on most broadly spread plant fungal pathogens at the tested concentrations. However, performing combinations of methylsulfonyl isothiocyanates with methylsulfonyl nitriles, thiocyanates or methylsulfinyl isothiocyanates can lead to fungitoxic activities.

Example 3

Examination of other aliphatic isothiocyanates led Applicants to test combinations of 6-Methylsulfonylhexyl isothiocyanates (6MSOOH) with: 6-methylsulfinylhexyl (6MSOH), 4-methylsulfinylbutyl (4MSOH), 8-methylsulfinyloctyl (8MSOH) and 8-methylsulfonyloctyl (8MSOOH) isothiocyanates for their fungitoxic effect on *Fusarium gramineum* (pathogen of barley and wheat) and *Phytophthora cactorum* (pathogen of 200 plant species).

Applicants had revealed that performing combinations with poorly active compounds could surprisingly lead to an increased fungitoxic activity on a large number of fungal pathogens. For example, both 6MSOOH and 6MSOH are not fungistatic to *Fusarium gramineum* in the dosage of 1500 μM. However, when applied in a mixture (combination of 6MSOOH and 6MSOH) they become highly fungitoxic with the effective dose at 116.8 μM that produces a quantitative effect in 50% of the population ($ED_{50}$). Similar effects were observed with the other combinations on both fungal species.

TABLE 3

Fungitoxic activity of isothiocyanates in diverse combinations against *P. cactorum* and *F. gramineum*.

| ED50 | P. cactorum | F. gramineum |
|---|---|---|
| 6MSOOH | <1500 | <1500 |
| 6MSOH | 667.27 | <1500 |
| 4MSOH | <1500 | 628.38 |
| 8MSOOH | 628.38 | 463.882 |
| 6MSOOH + 6MSOH | 207.17 | 116.84 |
| 6MSOOH + 4MSOH | 10 | 10 |
| 6MSOOH + 8MSOOH | 192.9 | 144.27 |

Conclusion: Combination of methylsulfonyl and methylsulfinyl isothiocyanates with different carbon chain lengths is revealing strong fungitoxic properties against a broad range of fungal pathogens. These results lead to the development of novel, natural organic products that can be used in agriculture, for example in the prevention of pathogen infections. Development of new combinations of products is particularly helpful in reducing the use of chemical pesticides as well as the doses. Besides, due to their high efficiency these new combinations are very helpful in promoting development of bio farming.

Example 4: Chemical Synthesis

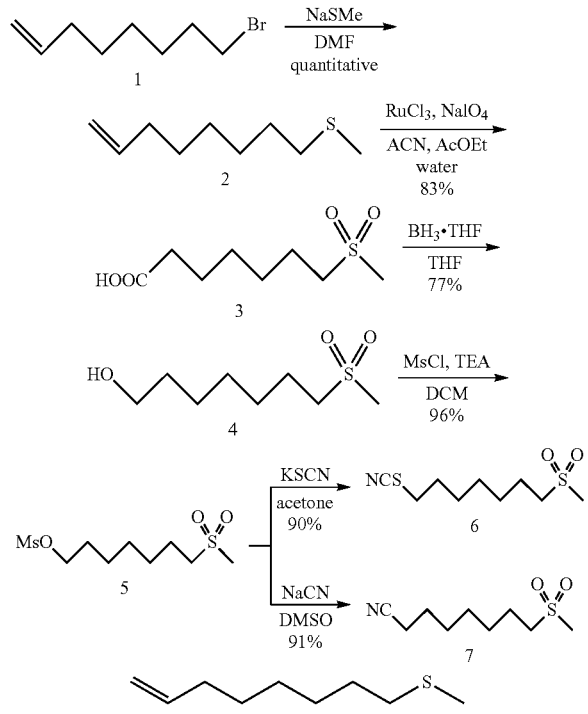

Methyl(oct-7-en-1-yl)sulfane (2). To a suspension of sodium thiomethoxide (3.23 g, 46.0 mmol) in dimethylformamide (85 ml) was added a solution of 8-bromooct-1-ene (8 g, 41.9 mmol) in dimethylformamide (195 ml) at 0° C. and the reaction mixture was stirred at room temperature for 14 h. The reaction mixture was diluted with saturated ammonium chloride solution and then extracted with ether (3×), combined organic layers were dried over sodium sulfate, filtered and concentrated under reduced pressure to get methyl(oct-7-en-1-yl)sulfane (7 g, 44 mmol), which was used for next step without any further purification.

1H NMR (300 MHz, Chloroform-d) δ 1.26-1.45 (m, 6H), 1.50-1.67 (m, 2H), 2.00-2.08 (m, 2H), 2.09 (s, 3H), 2.44-2.54 (m, 2H), 4.84-5.06 (m, 2H), 5.68-5.90 (m, 1H).

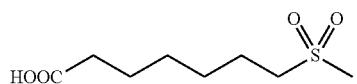

7-(methylsulfonyl)heptanoic acid (3). To an ice cooled solution of methyl(oct-7-en-1-yl)sulfane (2) in acetonitrile (139 ml) and ethyl acetate (139 ml) was added ruthenium trichloride trihydrate (197 mg, 0.834 mmol) followed by water (139 ml) and the mixture was stirred using mechanical stirrer. To this stirring solution was added sodium periodate (71.3 g, 334 mmol) in portions over 10 min. (careful, the possibility of explosion). After completion of addition, the mixture was stirred overnight at room temperature. The layers were separated and the organic layer was washed with sat. NaHCO$_3$, until the washings were showing basic pH. All the collected aqueous layers were washed with ethyl acetate and then acidified using 6N HCl, followed by extraction with ethyl acetate (3×). The combined organic layers were dried over sodium sulfate, filtered and concentrated under reduced pressure to get 7-(methylsulfonyl)heptanoic acid (3) (7.25 g, 34.8 mmol) in 83% yield. An analytical sample was prepared by triturating the crude in the ether, filtered and air dried and the remaining material was submitted to the next step without further purification. 1H NMR (300 MHz, Chloroform-d) δ 1.34-1.56 (m, 4H), 1.66 (m, 2H), 1.79-1.93 (m, 2H), 2.37 (t, J=7.3 Hz, 2H), 2.90 (s, 3H), 2.95-3.07 (m, 2H).

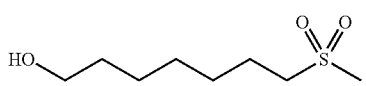

7-(methylsulfonyl)heptan-1-ol (4). To a solution of 7-(methylsulfonyl)heptanoic acid (3) (1 g, 4.80 mmol) in tetrahydrofuran (60 ml) was added borane tetrahydrofuran complex solution 1M in THF (14.40 ml, 14.40 mmol) dropwise at 0° C. under inert atmosphere and the reaction mixture was stirred at room temperature for 3 h. The reaction mixture was quenched by addition of saturated ammonium chloride solution and then the layers were separated, the aqueous layer was extracted with ethyl acetate (3×). The combined organic layers were dried over anhydrous sodium sulfate, filtered and concentrated under reduced pressure. The crude was purified by FC (Biotage, KP Sil-25 g, DCM, ethyl acetate, 0-100%) to get 7-(methylsulfonyl)heptan-1-ol (4) (0.72 g, 3.71 mmol, 77% yield) as a white solid.

1H NMR (300 MHz, Chloroform-d) δ 1.35-1.51 (m, 6H), 1.57 (m, 2H), 1.86 (m, 2H), 2.90 (s, 3H), 2.96-3.07 (m, 2H), 3.65 (td, J=6.5, 1.0 Hz, 2H).

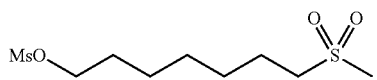 [SMILES: CS(=O)(=O)CCCCCCCOS(C)(=O)=O]

7-(methylsulfonyl)heptyl methanesulfonate (5). To a solution of 7-(methylsulfonyl)heptan-1-ol (4) (0.7 g, 3.60 mmol) in dichloromethane (36.0 ml) was added triethylamine (1.023 ml, 7.21 mmol) and the mixture was cooled to 0° C. To this mixture was added methanesulfonyl chloride (0.349 ml, 4.50 mmol) and then the reaction mixture was stirred at room temperature for 14 h. The reaction mixture was washed with 1M HCl solution and the aqueous layer was extracted with DCM. The combined organic layers were dried over sodium sulfate, filtered and concentrated under reduced pressure. The resulting crude was purified by FC (Biotage, KP Sil-25 g, DCM ethyl acetate, 0-40%) to get 7-(methylsulfonyl)heptyl methanesulfonate (5) (940 mg, 3.45 mmol, 96% yield) as a white solid.

1H NMR (300 MHz, Chloroform-d) δ 1.34-1.53 (m, 6H), 1.68-1.94 (m, 4H), 2.90 (s, 3H), 2.96-3.06 (m, 5H), 4.18-4.27 (m, 2H).

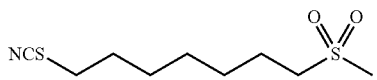

1-(methylsulfonyl)-7-thiocyanatoheptane (6). To a solution of 7-(methylsulfonyl)heptyl methanesulfonate (5) (0.2 g, 0.734 mmol) in acetone (5 ml) was added potassium thiocyanate (0.714 g, 7.34 mmol)) and the mixture was stirred at 60° C. in a sealed tube for 18 h. Then, the cooled reaction mixture was filtered through a fritted filter and the residue was washed with ether several times. The combined filtrates were concentrated to dryness and then purified by FC (Biotage, KP Sil-25 g, DCM, ethyl acetate, 0-40%) to get 1-(methylsulfonyl)-7-thiocyanatoheptane (6) (156 mg, 0.663 mmol, 90% yield) as a colorless oil.

1H NMR (300 MHz, Chloroform-d) δ 1.35-1.55 (m, 6H), 1.84 (m, 4H), 2.91 (s, 3H), 2.94 (t, J=7.2 Hz, 2H), 2.98-3.05 (m, 2H).

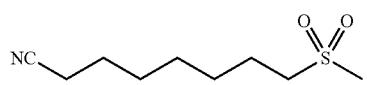

8-(methylsulfonyl)octanenitrile (7). To a solution of 7-(methylsulfonyl)heptyl methanesulfonate (5) (0.2 g, 0.734 mmol) in dimethyl sulfoxide (5 ml) was added sodium cyanide (0.180 g, 3.67 mmol) and the mixture was stirred at 60° C. in a sealed tube for 18 h. The cooled reaction mixture was diluted with ethyl acetate and washed with saturated ammonium chloride solution. The combined organic layers were dried over sodium sulfate, filtered and concentrated under reduced pressure. The resulting crude was purified by FC (Biotage, KP Sil-25 g, DCM, ethyl acetate, 0-40%) to get 8-(methylsulfonyl)octanenitrile (7) (0.136 g, 0.669 mmol, 91% yield) as a colorless oil.

1H NMR (300 MHz, Chloroform-d) δ 1.33-1.55 (m, 6H), 1.60-1.74 (m, 2H), 1.79-1.94 (m, 2H), 2.35 (td, J=7.0, 0.6 Hz, 2H), 2.90 (s, 3H), 2.96-3.05 (m, 2H).

Synthesis of 5MSOOH

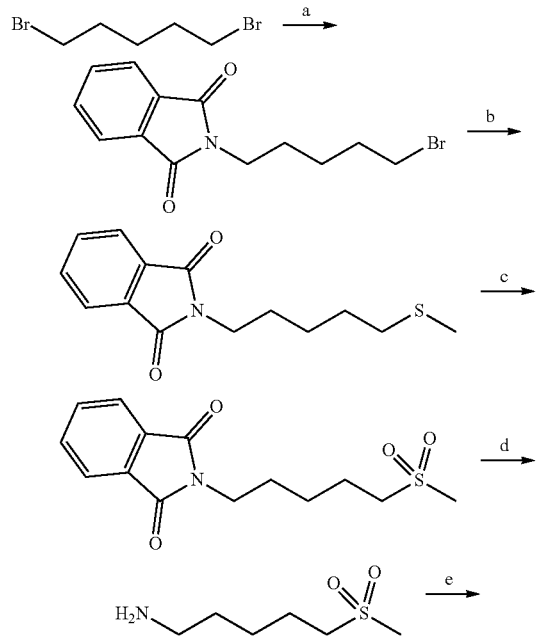

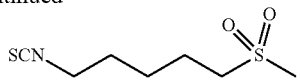

Conditions:
a. phthalimide, N-benzyl-N, N-diethylethanaminium chloride, K2CO3, acetone, 24° C., 2 days; 38%,
b. NaSMe, DMF, 0-RT° C., 16 h; quantitative yield;
c. mCPBA, DCM, 0° C., 14 h, quantitative yield;
d. NH2NH2•H2O, MeOH, 24° C., 16 h; 92%;
e. thiophosgene, NaOH, CHCl3, 0° C., 2 h, 59%

2-(5-bromopentyl)isoindoline-1,3-dione (SVB-18-025)

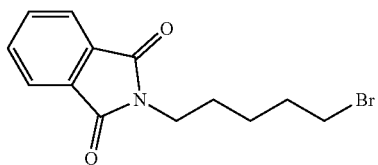 [SMILES: O=C1c2ccccc2C(=O)N1CCCCCBr]

To a solution of PHTHALIMIDE (3 g, 20.39 mmol) in acetone (102 ml) was added N-benzyl-N,N-diethylethanaminium chloride (0.511 g, 2.243 mmol), K2CO3 (8.45 g, 61.2 mmol), and 1,5-dibromopentane (14.07 g, 61.2 mmol) and the reaction mixture was stirred at rt for 14 h. The reaction mixture was concentrated to dryness and the residue was resuspended in water, extracted with DCM (3×), combined organic layers were dried over sodium sulfate, filtered and concentrated under reduced pressure to get crude. This was purified using FC (SiO2, hexane, ethyl acetate, 0-40%) to get 2-(5-bromopentyl)isoindoline-1,3-dione (2.3 g, 7.77 mmol, 38.1% yield) as a colorless oil.

1H NMR (300 MHz, Chloroform-d) δ 7.89-7.80 (m, 2H), 7.77-7.66 (m, 2H), 3.75-3.63 (m, 2H), 3.44-3.31 (m, 2H), 1.99-1.84 (m, 2H), 1.79-1.63 (m, 2H), 1.60-1.42 (m, 2H).

2-(5-(methylthio)pentyl)isoindoline-1,3-dione (SVB-18-033)

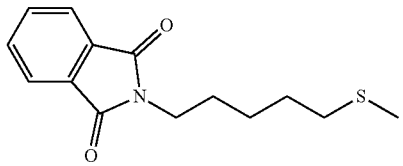 [SMILES: CSCCCCCN1C(=O)c2ccccc2C1=O]

To a suspension of NaSMe (0.833 g, 11.89 mmol) in DMF (21.83 ml) was added a solution of 2-(5-bromopentyl)isoindoline-1,3-dione (3.2 g, 10.80 mmol) in DMF (50.2 ml) at 0° C. and the reaction mixture was stirred rt for 14 h. The reaction mixture was diluted with NH4Cl solution and then extracted with ether (3×), combined organic layers were dried over sodium sulfate, filtered and concentrated under reduced pressure to get crude. This was used for next step without any further purification.

1H NMR (300 MHz, Chloroform-d) δ 7.90-7.80 (m, 2H), 7.78-7.66 (m, 2H), 3.74-3.63 (m, 2H), 2.54-2.42 (m, 2H), 2.08 (s, 3H), 1.80-1.57 (m, 5H), 1.52-1.37 (m, 2H).

2-(5-(methylsulfonyl)pentyl)isoindoline-1,3-dione
(SVB-18-038)

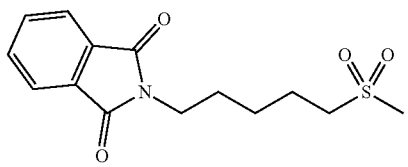 [SMILES: CS(=O)(=O)CCCCCN1C(=O)c2ccccc2C1=O]

To a solution of 2-(5-(methylthio)pentyl)isoindoline-1,3-dione (2.8 g, 10.63 mmol) in DCM (53.2 ml) at 0° C. was added m-CPBA (6.55 g, 26.6 mmol) in portions and the reaction mixture was stirred at rt for 14 h. To the reaction was added 100 ml, 1:1 solution of saturated NaHCO$_3$ and 10% sodium thiosulphate solution and this was stirred for 1 h, the layers were separated and the aqueous layer was extracted with DCM (3×), combined organic layers were dried over sodium sulfate, filtered and concentrated to get 2-(5-(methylsulfonyl)-pentyl)-isoindoline-1,3-dione (3.1 g, 10.50 mmol, 99% yield) as a white solid.

1H NMR (300 MHz, Chloroform-d) δ 7.89-7.82 (m, 2H), 7.77-7.68 (m, 2H), 3.71 (t, J=7.0 Hz, 2H), 3.07-2.95 (m, 3H), 2.93-2.87 (m, 4H), 1.99-1.86 (m, 2H), 1.82-1.67 (m, 2H), 1.61-1.43 (m, 2H).

5-(methylsulfonyl)pentan-1-amine (SVB-18-042)

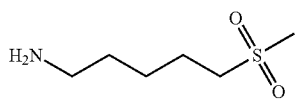

To a solution of 2-(5-(methylsulfonyl)pentyl)isoindoline-1,3-dione (3.1 g, 10.50 mmol) in methanol (52.5 ml) at rt was added hydrazine hydrate (1.020 ml, 20.99 mmol) and the reaction mixture was stirred at rt for 2 h. The reaction mixture was concentrated under vacuum and then the residue was suspended in 1M KOH solution, extracted with ethyl acetate (3×) combined organic layers were dried over sodium sulfate, filtered and concentrated under reduced pressure to get 5-(methylsulfonyl)pentan-1-amine (1.6 g, 9.68 mmol, 92% yield) as a white solid. this material was clean enough to use for next reaction.

1-isothiocyanato-5-(methylsulfonyl)pentane
(SVB-18-048)

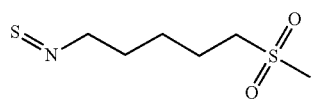

To a solution of 5-(methylsulfonyl)pentan-1-amine (0.25 g, 1.513 mmol) in chloroform (7.56 ml) at 0° C. was added thiophosgene (0.150 ml, 1.967 mmol) followed by addition of 5% aqueous NaOH and the mixture was stirred at 0° C. for 2 h. The reaction mixture was diluted with water and then the layers were separated, the aqueous layer was extracted with DCM (3×). Combined organic layers were dried over sodium sulfate filtered and concentrated under reduced pressure to get crude. This was purified using FC(SiO2, hexane, ethyl acetate, 0-40%) to get 1-isothiocyanato-5-(methylsulfonyl)pentane (0.185 g, 0.892 mmol, 59.0% yield).

1H NMR (300 MHz, Chloroform-d) δ 3.56 (t, J=6.3 Hz, 2H), 3.10-3.00 (m, 2H), 2.93 (d, J=0.7 Hz, 3H), 1.98-1.86 (m, 2H), 1.83-1.70 (m, 2H), 1.68-1.53 (m, 2H).

Example 5

Investigation of natural combinations of isothiocyanates with diverse carbon lengths and sulfinyl or sulfonyl groups led Applicants to identify highly efficient antifungal mixtures of compounds. Applicants used the effective dose that produces a quantitative effect in 95% of the population (ED95) at the maximal concentration of 1500 µM to investigate the fungitoxic activity of analyzed compounds. Applicants have chosen the second most broadly spread plant fungal pathogens to perform toxicity assay—*Botrytis cinerea* (pathogen of 1400 plant species), due to its worldwide distribution and to not sufficient amount of efficient organic products to treat this fungal pathogen.

Initially, Applicants has chosen 4 compounds that were shown to be fungitoxic on a broad number of fungal pathogens e.g. *Phytophthora infestans, Fusarium gramineum*: 5-methylsulfonyl-pentyl- (5MSOOH), 5-methylsulfinyl-pentyl- (5MSOH), 8-methylsulfonyl-octyl-(8MSOOH) and 8-methylsulfinyl-octyl- (8MSOH) isothiocyanates. However, none of these single compounds revealed fungitoxic effect on *Botrytis cinerea*. To enhance anti-*Botrytis* properties Applicants performed combinations with 5MSOOH, 5MSOH, 8MSOOH and 8MSOH compounds. Surprisingly, only two combinations revealed anti-fungal properties: first, 8MSOOH with 8MSOH (ED95 of 1400 µM) and second, 8MSOH with 5MSOOH that became highly toxic to *B. cinerea* in a dosage of 550 µM. Results of single molecules and their combinations are presented in Table 4.

TABLE 4

Fungitoxic activity of diverse isothiocyanates
(combined and single molecules) against *Botrytis cinerea*.

| ED$_{95}$ | *Botrytis cinerea* |
|---|---|
| 5MSOOH | <1500 |
| 5MSOH | <1500 |
| 8MSOOH | <1500 |
| 8MSOH | <1500 |
| 5MSOOH + 5MSOH | <1500 |
| 8MSOOH + 8MSOH | 1400 |
| 8MSOOH + 5MSOH | <1500 |
| 8MSOOH + 5MSOOH | <1500 |
| 8MSOH + 5MSOOH | 550 |
| 8MSOH + 5MSOH | <1500 |

Conclusion: By-products of glucosinolates such as methylsulfonyl and methylsulfinyl isothiocyanates used separately reveal no strong fungitoxic activity on the most broadly spread plant fungal pathogen—*Botrytis cinerea* at the tested concentrations. However, performing combinations of compounds having diverse carbon lengths and presenting sulfinyl or sulfonyl groups lead to strong fungitoxic activities at low dosages thus enhancing the fungitoxic effect compared to combinations of molecules having the same carbon lengths and presenting only differences in term of functional groups (i.e. sulfinyl and sulfonyl groups).

Example 6

Examination of the fungitoxic properties of single and combined aliphatic isothiocyanates led Applicants to in depth investigation activities of 8-methylsulfonyl-octyl- (8MSOOH) and 8-methylsulfinyl-octyl- (8MSOH) isothiocyanates. Applicants performed fungitoxic studies using: *Fusarium gramineum* (pathogen of barley and wheat), *Phytophthora infestans* (pathogen of Solanaceae) and *Guignardia bidwellii* (pathogen of grapes).

Applicants measured a fungitoxic effect caused by single and combined molecules of 8MSOOH and 8MSOH in 50% of the fungal population ($ED_{50}$). Results of this assay are included in Table 5.

TABLE 5

Fungitoxic activity of isothiocyanates in various combinations against *P. infestans*, *F. gramineum* and *G. bidwellii*.

| ED50 | P. infestans | F. gramineum | G. bidwellii |
|---|---|---|---|
| 8MSOH | 26.36 | 292.03 | 30.38 |
| 8MSOOH | 350 | 22.18 | 463.88 |
| 8MSOOH + 8MSOH | 10 | 61.73 | 40.2 |

Conclusion: Combination of molecules with the same carbon chain length methylsulfonyl and methylsulfinyl isothiocyanates is not enhancing fungitoxic properties in *F. gramineum* and *G. bidwellii*, but turned to be efficient for *P. infestans*.

Example 7

Fungitoxic activities of combined isothiocyanates in three necrotrophic fungal species Applicants examined fungitoxic activities of combined isothiocyanates in three necrotrophic fungal species, i.e. *Alternaria radicina* (class: Dothideomycetes; order: Pleosporales; host: carrot), *Fusarium gramineum* (class: Sordariomycetes; order: Hypocreales; host: cereals) and *Plectosphaerella cucumerina* (class: Sordariomycetes; order: Glomerellales; host: tomato and cucurbits). Overall, a total of 133 combinations were tested on the three fungal species.

Isothiocyanates were obtained from SpiroChem (Basel, Switzerland) and LKT LABS (Minnesota, United States of America). All the obtained compounds were dissolved in dimethyl sulfoxide (DMSO). Fungal strains used for in vitro fungal bioassay were obtained from the mycotheca of Agroscope (www.mycoscope.bcis.ch).

Fungitoxic activities were tested in 48 well tissue culture plates. In more details, plant fungal pathogens were inoculated on PDA implemented with isothiocyanates that were preliminary dissolved to various concentration (10, 150, 250, 375, 500, 700, 850 μM) in PDB. 2 mm agar plug (Dufour et al. 2015) of a fungal pre-culture were placed on each well, 3 biological replicates were used for each concentration. Plates were incubated for the period of one week in the phytotron (80% relative humidity, constant temperature of 23° C., under alternating 16 h day and 8 h night cycles). Mycelia growth was measured after 7 days using ImageJ (http://imagej.net/Welcome), $ED_{50}$ was evaluated as described in Schnee et al., 2013. Synergistic fungitoxic activities was then estimated as in Chou (2006), and the CompuSyn software (www.combosyn.com) was used to determine the Combination Index (CI) for combinations of two molecules and the presence of synergism (CI<1). The results obtained for the best combinations for each fungal species are summarized in Table 6, 7 and 8. It shows the $ED_{50}$ (in μM) obtained for the two molecules alone, for the combination of them (always smaller), and the lower Combination Index for at least one given concentration in a range varying from 10 to 850 μM. All CI listed in the table below being lower than 0.26, it indicates that the combined molecules have strong synergisms and are efficient against the tested fungal species.

Additional molecules used in these combinations are: 1-(isothiocyanatomethyl)-3-(4-(methylsulfinyl)butyl)benzene (8ASOH), 1-(isothiocyanatomethyl)-3-(4-(methylsulfonyl)butyl)benzene (8ASOOH), (E)-1-isothiocyanato-8-(methylsulfinyl)oct-2-ene (8CSOH), 1-(ethylsulfinyl)-8-isothiocyanatooctane (8ESOH), 1-(ethylsulfonyl)-isothiocyanatooctane (8ESOOH), 1-Isothiocyanato-3-(methylsulfinyl)-propane (3MSOH), 1-Isothiocyanato-3-(methylsulfonyl)-propane (3MSOOH), 1-Isothiocyanato-9-(methylsulfinyl)-nonane (9MSOH) and 1-Isothiocyanato-9-(methylsulfonyl)-nonane (9MSOOH).

TABLE 6

Best combination of molecules against *Alternaria Radicina* (molecules for which 850 is mentioned for EC50, are those with no fungitoxic activity in the tested range).

| Combination | EC50 Molecule 1 | EC50 Molecule 2 | EC50 combination | CI combination |
|---|---|---|---|---|
| 8ASOH/8ASOOH | 723.3 | 850 | 156.08 | 0.02872 |
| 8CSOH/8ESOH | 704.24 | 472.4 | 390 | 0.08735 |
| 8CSOH/8ESOOH | 472.4 | 850 | 474.46 | 0.115 |
| 8CSOH/3MSOOH | 704.24 | 468.89 | 479.2 | 0.02991 |
| 8CSOH/7MSOH | 704.24 | 536.96 | 534.04 | 0.08249 |
| 8CSOH/3MSOH | 704.24 | 786.17 | 625.78 | 0.25268 |

TABLE 7

Best combination of molecules against *Fusarium gramineum* (molecules for which 850 is mentioned for EC50, are those with no fungitoxic activity in the tested range).

| Combination | EC50 Molecule 1 | EC50 Molecule 2 | EC50 combination | CI combination |
|---|---|---|---|---|
| 8MSOH/3MSOOH | 316.78 | 386.88 | 252.41 | 0.24857 |
| 8MSOH/7MSOH | 316.78 | 586.15 | 258.16 | 0.16426 |
| 8MSOH/9MSOH | 316.78 | 552.9 | 263.27 | 0.15388 |
| 8MSOH/6MSOH | 316.78 | 850 | 266.17 | 0.25732 |
| 8CSOH/8MSOH | 850 | 316.78 | 274.62 | 0.13763 |
| 8CSOH/3MSOOH | 850 | 386.88 | 282.16 | 0.10929 |
| 8MSOH/9MSOOH | 316.78 | 850 | 283.52 | 0.13736 |
| 8CSOH/3MSOH | 850 | 525.24 | 383.96 | 0.04368 |
| 8CSOH/7MSOH | 850 | 586.15 | 389.42 | 0.03555 |
| 8ESOH/7MSOH | 533.3 | 586.15 | 414.39 | 0.12419 |
| 8ESOH/3MSOH | 533.3 | 525.24 | 455.21 | 0.15703 |
| 8MSOOH/7MSOH | 850 | 586.15 | 540.78 | 0.06049 |

TABLE 8

Best combination of molecules against *Plectosphaerella cucumerina* (molecules for which 850 is mentioned for EC50, are those with no fungitoxic activity in the tested range).

| Combination | EC50 Molecule 1 | EC50 Molecule 2 | EC50 combination | CI combination |
|---|---|---|---|---|
| 8CSOH/7MSOH | 272.83 | 337.32 | 145.68 | 0.18832 |
| 8MSOOH/3MSOH | 850 | 626.83 | 483.44 | 0.09631 |
| 8MSOOH/3MSOOH | 850 | 536.05 | 521.17 | 0.03061 |

Example 8

In vivo fungal bioassay with *Plasmopara viticola* (Class: Oomycetes; Order: Peronosporales; Biotrophic pathogen of Grapevine)

1-Isothiocyanato-8-(methylsulfonyl)-octane and 1-Isothiocyanato-8-(methylsulfinyl)-octane were obtained from SpiroChem (Basel, Switzerland). The compounds were dissolved in dimethyl sulfoxide (DMSO).

Leaf discs were collected from the 4th and 5th leaves of *Vitis vinifera* cv. Cabernet Sauvignon washed under water beforehand. For each concentration (0, 100, 250, 500, 750 and 1000 µM), 10 dry leaf discs were placed in Petri dishes on wet filter papers. Leaf discs were sprayed with the different concentrations of active molecules and dried under the sterile hood. Once dry, they were sprayed with a solution of *Plasmopara viticola* ($10^5$ spores/mL) and Petri dishes were closed and incubated in dark conditions. After 1 h, Petri dishes were randomly placed on the bench under normal day/night conditions. Infection percentages were calculated after 7 days as in Schnee et al. (2013).

TABLE 9

Fungitoxic activity of combined isothiocyanates against *Plasmopara viticola*.
*Plasmopara viticola*

| Combination | EC50 |
|---|---|
| 8MSOH/8MSOOH | 94.2 |

The tested combination revealed a strong efficacy against this biotrophic fungal pathogen (EC50: 94.2)

Example 9

*Tricophyton rubrum* (Class: Eurotiomycetes; Order: Onygenales; skin and nails human pathogen)

1-Isothiocyanato-8-(methylsulfonyl)-octane and 1-Isothiocyanato-8-(methylsulfinyl)-octane were obtained from SpiroChem (Basel, Switzerland). The compounds were dissolved in dimethyl sulfoxide (DMSO).

Fungitoxic activity was tested in 48 well tissue culture plates. Tricophyton *rubrum* was inoculated on PDA implemented with isothiocyanates that were preliminary dissolved to various concentration (10, 150, 250, 375, 500, 700, 850 µM) in PDB. 2 mm agar plugs (Dufour et al. 2015) of a fungal pre-culture were placed on each well, 3 biological replicates were used for each concentration. Plates were incubated for the period of one week in a phytotron (80% relative humidity, constant temperature of 23° C., under alternating 16 h day and 8 h night cycles). Mycelia growth was measured after 7 days using ImageJ (http://imagej.net/Welcome), $EC_{50}$ was evaluated as described in Schnee et al., 2013.

TABLE 10

Fungitoxic activity of combined isothiocyanates against *Tricophyton rubrum*
*Tricophyton rubrum*

| Combination | EC50 |
|---|---|
| 8MSOH/8MSOOH | 275.2 |

Example 10

*Thamnidium elegans* (Class Zygomycetes; Order Mucorales; stored meat)

1-Isothiocyanato-8-(methylsulfonyl)-octane and 1-Isothiocyanato-8-(methylsulfinyl)-octane were obtained from SpiroChem (Basel, Switzerland). The compounds were dissolved in dimethyl sulfoxide (DMSO).

Fungitoxic activity was tested in 48 well tissue culture plates. Thamnidium *elegans* was inoculated on PDA implemented with isothiocyanates that were preliminary dissolved to various concentration (10, 150, 250, 375, 500, 700, 850 µM) in PDB. 2 mm agar plugs (Dufour et al. 2015) of a fungal pre-culture were placed on each well, 3 biological replicates were used for each concentration. Plates were incubated for the period of one week in a phytotron (80% relative humidity, constant temperature of 23 OC, under alternating 16 h day and 8 h night cycles). Mycelia growth was measured after 7 days using ImageJ (http://imagej.net/Welcome), EC50 was evaluated as described in Schnee et al., 2013.

TABLE 11

Fungitoxic activity of combined isothiocyanates against *Thamnidium elegans*.

| Combination | EC50 |
|---|---|
| 8MSOH/8MSOOH | 395.0 |

The tested combination revealed to be efficient against this fungal species developing on stored meat (EC50: 395).

List of molecules used in the examples

| Molecule abbreviation | IUPAC name |
|---|---|
| 7MSOH | 1-Isothiocyanato-7-(methylsulfinyl)-heptane |
| 8MSOOH | 1-Isothiocyanato-8-(methylsulfonyl)-octane |
| 8MSOH | 1-Isothiocyanato-8-(methylsulfinyl)-octane |
| 8MSOON | 8-(methylsulfonyl)octylnitrile |
| 6MSOH | 1-Isothiocyanato-6-(methylsulfinyl)-hexane |
| 4MSOH | 1-Isothiocyanato-4-(methylsulfinyl)-butane |
| 6MSOOH | 1-Isothiocyanato-6-(methylsulfonyl)-hexane |
| 5MSOOH | 1-Isothiocyanato-5-(methylsulfonyl)-pentane |
| 5MSOH | 1-Isothiocyanato-5-(methylsulfinyl)-pentane |
| 8ASOH | 1-(isothiocyanatomethyl)-3-(4-(methylsulfinyl)butyl)benzene |
| 8ASOOH | 1-(isothiocyanatomethyl)-3-(4-(methylsulfonyl)butyl)benzene |
| 8CSOH | (E)-1-isothiocyanato-8-(methylsulfinyl)oct-2-ene |
| 8ESOH | 1-(ethylsulfinyl)-8-isothiocyanatooctane |
| 8ESOOH | 1-(ethylsulfonyl)-8-isothiocyanatooctane |
| 3MSOOH | 1-Isothiocyanato-3-(methylsulfonyl)-propane |
| 3MSOH | 1-Isothiocyanato-3-(methylsulfinyl)-propane |
| 9MSOH | 1-Isothiocyanato-9-(methylsulfinyl)-nonane |
| 9MSOOH | 1-Isothiocyanato-9-(methylsulfonyl)-nonane |

REFERENCES

1. Schreiner R P, Koide R T. 1993a. Antifungal compounds from the roots of mycotrophic and non-mycotrophic plant species. New Phytol. 123:99-105.
2. Dufour V, Stahl M, Baysse C. 2015. The antibacterial properties of isothiocyanates. *Mycrobiol.* 161(Pt 2):229-43.
3. Lambrix V, Reichelt M, Mitchell-Olds T, Kliebenstein D J, Gershenzon J. 2001. The Arabidopsis epithiospecifier protein promotes the hydrolysis of glucosinolates to nitriles and influences *Trichoplusia ni* herbivory. *Plant Cell*. 13(12):2793-807.
4. Schnee S, Queiroz E F, Voinesco F, Marcourt L, Dubuis P-H, Wolfender J-L, Gindro K. 2013. *Vitis vinifera* canes, a new source of antifungal compounds against *Plasmopora viticola, Erysiphe necator*, and *Botrytis cinerea*. J. Agric. Food Chem. 61(23):5459-67.
5. Chou T C. 2006. Theoretical basis, experimental design, and computerized simulation of synergism and antagonism in drug combination studies. Pharmacol Rev 58:621-681, 2006.

The invention claimed is:

1. A fungicide composition comprising the combination of at least two compounds, wherein the combination of at least two compounds is a mixture of 1-Isothiocyanato-8-(methylsulfonyl)-octane and 1-Isothiocyanato-8-(methylsulfinyl)-octane or a mixture of 1-Isothiocyanato-8-(methylsulfonyl)-octane and 1-Isothiocyanato-9-(methylsulfinyl)-nonane,
wherein the $EC_{50}$ of the combination is lower than the $EC_{50}$ of each component of the combination against a fungal pathogen and/or wherein the combination index (CI) of the combination is <1.

2. A method for the prevention or treatment of fungal pathogens in plants comprising treating the plants with a fungicidal composition according to claim 1.

3. The method according to claim 2, wherein the composition is fungitoxic and/or fungistatic in plants.

4. The method according to claim 2, in plant cultures in the field or for in vitro implementation thereof.

5. The fungicide composition according to claim 1, in combination with acceptable carriers or diluents.

6. The fungicide composition according to claim 1, wherein the fungicide composition is active against plant fungal pathogens selected from the phylum comprising Basidiomycota, Zygomyceta, Oomycota or Ascomycota.

7. A disinfectant composition in oral hygiene or sanitary articles comprising the combination of 1-Isothiocyanato-8-(methylsulfinyl)-octane/1-Isothiocyanato-8-(methylsulfonyl)-octane,
wherein the $EC_{50}$ of the combination is lower than the $EC_{50}$ of each component of the combination against a fungal pathogen and/or wherein the combination index (CI) of the combination is <1.

8. The disinfectant composition according to claim 7, wherein the oral hygiene articles are selected from the group consisting of a dentifrice, a lozenge, a liquid or powdered mouthwash, a coating solution, a halitosis preventing agent, and a chewing gum.

* * * * *